US006921840B1

(12) United States Patent
Kung

(10) Patent No.: US 6,921,840 B1
(45) Date of Patent: Jul. 26, 2005

(54) SPECT IMAGING AGENTS FOR SEROTONIN TRANSPORTERS

(75) Inventor: Hank F. Kung, Wynnewood, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/959,581

(22) PCT Filed: Apr. 30, 1999

(86) PCT No.: PCT/US99/09344

§ 371 (c)(1),
(2), (4) Date: Feb. 8, 2002

(87) PCT Pub. No.: WO00/66537

PCT Pub. Date: Nov. 9, 2000

(51) Int. Cl.[7] ............................................. C07C 213/00
(52) U.S. Cl. ..................................................... 564/430
(58) Field of Search .............................. 424/1.81, 1.85; 568/58; 564/430

(56) References Cited

U.S. PATENT DOCUMENTS

| 5,071,636 | A |   | 12/1991 | Yamauchi et al. |          |
|-----------|---|---|---------|-----------------|----------|
| 5,324,502 | A | * | 6/1994  | Green et al.    | 424/1.81 |
| 5,688,485 | A |   | 11/1997 | Harris          |          |
| 5,783,171 | A |   | 7/1998  | Gustavson et al.|          |

FOREIGN PATENT DOCUMENTS

| DE | 41 28183 C1    | 1/1993  |
| EP | 0 402 097 A1   | 12/1990 |
| WO | WO 92/19210 A  | 11/1992 |
| WO | WO 93/12080    | 6/1993  |
| WO | WO 97/17325    | 5/1997  |

OTHER PUBLICATIONS

Journal of Medicinal Chemistry by Oya et al vol. 42, No. 3 pp 333–335 Feb. 1999.*
CA:132:134139 abs of Euro. Journ. of Nuclear Med. by Kung et al 26(8) pp 844–853 1999.*
CA:69:110468 abs of Helvetica Chimica Acta by Erlenmeyer et al 51(7) pp 1795–7 1968.*
CA:94:29962 abs of J of Chem. Soc., Perkin Trans. 2: Phys. Organic Chem. (10) pp1529–43 1980.*
CA:106:58728 abs of J. Chem Soc., Faraday Trans. 2: Molecular and Chemical Phys. by Abou–Gamra et al 82(12) pp 2337–50 1986.*
CA:122:176981 abs of Inorganic Chem. by Bossard et al 34(6) pp 1524–7 1995.*
Oya S., et al., "A new single–photon emission computed tomography imaging agent for serotonin transporters: (123I) IDAM, 5–Iodo–2–((dimethylamino)methyl)–phenyl)thio)benzyl Alcohol", J. Med. Chem., 42(2):333–335, American Chemical Society (1999).
Supplementary European Search Report for Application No. 99918906 (Apr. 17, 2003).

Ferris, R.M., et al., "Pharmacological Properties of 403U76, a New Chemical Class of 5–Hydroxytryptamine– and Noradrenaline–reuptake Inhibitor," J. Pharm. Pharmacol. 47:775–781, (1995).
Maryanoff, B.E., et al., "Pyrroloisoquinoline Antidepressants. 2. In–Depth Exploration of Structure–Activity Relationships," J. Med. Chem. 30:1433–1454, American Chemical Society (1987).
Maryanoff, B.E., et al., "Pyrroloisoquinoline Antidepressants. 3. A Focus on Serotonin," J. Med. Chem. 33:2793–2797, American Chemical Society (1990).
Shank, R.P., et al., "McN–5652: A Highly Potent Inhibitor of Serotonin Uptake," J. Pharm. Exp. Ther. 247:1032–1038, The American Society for Pharmacology and Experimental Therapeutics (1988).
Szabo, Z., et al., "Positron Emission Tomography of 5–HT Transporter Sites in the Baboon Brain with [$^{11}$C] McN5652," J. Cereb. Blood Flow Metab. 15:798–805, Lippincott–Raven Publishers (1995).
Szabo, Z., et al., "Positron Emission Tomography Imaging of Serotonin Transporters in the Human Brain Using [$^{11}$C] (+) McN5652," Synapse 20:37–43, Wiley–Liss, Inc. (1995).
Szabo, Z., et al., "Positron emission tomography of 5–HT reuptake sites in the human brain with C–11 McN5652 Extraction of characteristic images by artificial neural network analysis," Behav. Brain Res. 73:221–224, Elsevier Science B.V. (1996).
International Search Report for International Patent Application No. PCT/US99/09344, mailed Aug. 25,1999.

(Continued)

Primary Examiner—Johann Richter
Assistant Examiner—Chukwuma Nwaonicha
(74) Attorney, Agent, or Firm—Sterne, Kessler, Goldstein & Fox P.L.L.C.

(57) ABSTRACT

The present invention is directed to compounds of Formula (I) or pharmaceutically acceptable salts thereof; wherein X is hydrogen, Cl, Br, I, $NO_2$, $NR^3R^4$ or —L—Ch; Y is hydrogen, —$CH_2OR^5$, —$CH_2NCH_3R^1$, $NO_2$, $NR^3R^4$ or —L—Ch; Y' is hydrogen, —$CH_2OH^5$, —$CH_2NCH_3R^1$, $NO_2$, $NR^3R^4$ OR —L—Ch; provided that at least one of the Y or Y' is —$CH_2NCH_3R^1$; Z is S, O, $NR^6$ $CR^7R^8$, C(O) or —C(=$CR^7R^8$)-; A is hydrogen, Cl, I, Br or —L—Ch; $R^1$ is hydrogen, $C_1$–$C_5$ alkyl, $C_3$–$C_8$ cycloalkyl $C_{1-5}$ alkylcarbonyl, ($C_3$–$C_8$ cycloalkyl) carbonyl, pnenyl, benzyl, naphthyl, naphthylmethyl or L—Ch; $R^2$ is hydrogen or methyl; and $R^3$–$R^8$ are as defined herein. Radiolabeled compounds of the invention are useful as selective serotonin transporter (SERT) imaging agents for single photon emission tomography (SPECT). As such the compounds are useful for studying the underlying pharmacology and interaction of specific serotinin reuptake site inhibitors (SSRI), commonly used antidepressants, at the SERT sites in the human brain. Certain compounds of the invention, including IDAM (5-iodo-2[[2-2-[(dimethylamino)methyl]phenyl]thio]benzylalcohol) display affinity to SERT sites and show more high selectively for SERT over NET and DAT.

13 Claims, 8 Drawing Sheets

OTHER PUBLICATIONS

STN Database, Chemical Abstracts, Accession No. 1971:22490, abstract of Freter, K., et al., "New group of anorexigenic compounds," *J. Med. Chem.* 13:1228–1230, American Chemical Society (1970).

STN Database, Chemical Abstracts, Accession No. 1991:228508, English language abstract of EP 0 402 097 A1.

* cited by examiner

FIG.4A
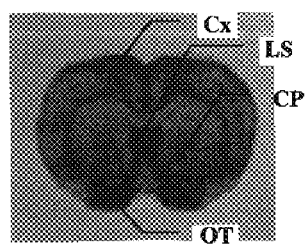
FIG.4B
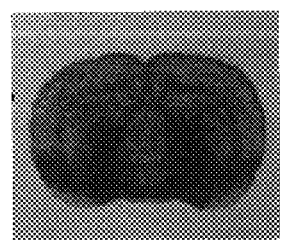
FIG.4C
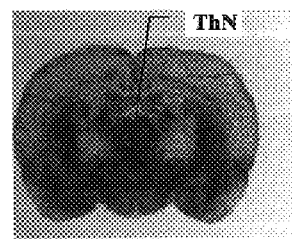
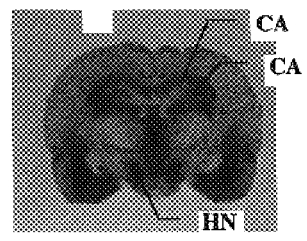
FIG.4D
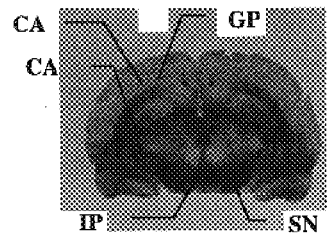
FIG.4E
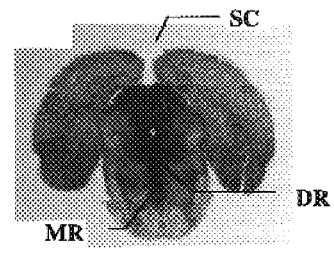
FIG.4F

| Ia-c | IIa-c | IIIa-c |
|---|---|---|
| $R_1$: a: $CH_3$, b: $C_2H_5$, c: $C_3H_7$ | $R_1$: H | $R_1$: $CH_3$ |
| $R_2$: $CH_3$ | $R_2$: $CH_3$ | $R_2$: $CH_3$ |
| $R_3$: $CH_3$ | $R_3$: a: $CH_3$ | $R_3$: a: $CH_3$ |
|  | b: $C_2H_5$ | b: $C_2H_5$ |
|  | c: $C_3H_7$ | c: $C_3H_7$ |

SPECT IMAGING AGENTS FOR SEROTONIN TRANSPORTERS

This application is a national phase entry of International Patent Application No. PCT/US99/09344, filed Apr. 30, 1999, which published under PCT Article 21 (2) in English as Publication No. WO 00/66537.

STATEMENT AS TO RIGHTS TO INVENTIONS MADE UNDER FEDERALLY-SPONSORED RESEARCH AND DEVELOPMENT

Part of the work performed during development of this invention utilized U.S. Government funds under NIH Grant No. NS-35120. The U.S. Government has certain rights in this invention.

BACKGROUND OF THE INVENTION

1. Field of the Invention

This invention relates to novel compounds for CNS neurotransmitter systems especially for the neurotransmitter serotonin, which can be utilized to image neurotransmitter reuptake systems in the brain.

2. Related Art

Depression, with its related conditions, is one of the most common mental disorders in the United States. It is estimated that about five percent of the adult population experiences a depressive episode in their lifetime that requires antidepressive drug therapy. A chemical in the human brain, called serotonin, has been linked with depression and with other psychiatric disorders such as eating disorders, alcoholism, pain, anxiety and obsessive-compulsive behavior.

Serotonin (5-FT) is an essential neurotransmitter for the normal function of the central nervous system. This neurotransmission system in the brain controls various important behaviors, including sleep awake cycle, mood, temperature, appetite, etc. In addition, several commonly used anti-anxiety drugs (Frazer, A. and J. G. Hensler, *Ann. NY Acad. Sci.* 600:460–475 (1990); Gozlan, H. and M. Hamon, *Anxiety: Neurobiol., Clinic and Ther. Persp.* 232:141–150 (1993)) and antidepressants (Frazer, A., *J. Clin. Psychiatry* 6:9–25 (1997), Coryell, W., *J. Clin Psychiatry* 1:22–27 (1998); Heninger, G. R. et al., *Pharmacopsychiatry* 29(1):2–11 (1996); Fuller, R. W., *Prog. Drug Res.* 45:167–204 (1995)) interact specifically with serotonin neurotransmission. Pharmacological actions of the antidepressants (selective serotonin reuptake inhibitors; SSRI), such as fluoxetine (Wong, D. T. and F. P. Bymaster, *Biology* 363:77–95 (1995)), paroxetine (Holliday, S. M. and G. L. Plosker, *Drugs Aging* 3(3)278–299 (1993)) and sertraline (Lasne, M. C. et al., *Int. J. Rad Appl. Inst.—Part A, Applied Rad Isot.* 40(2):147–151 (1989)), are based on blockade of presynaptic transporters serotonin. Thus, studies of radioligand binding to serotonin transporter (SERT) may provide valuable information of these sites in normal and various disease states. Several tritiated ligands including imipramine (Raisman, R. et al. *Eur. J. Pharmacol.* 54:307–308 (1979)), citalopram (D'Amato, R. et al. *Pharmacol. Exp. Ther.* 242 (1):364–371 (1987)), paroxetine (Habert, E., et al. *Eur. J. Pharmacol.* 118(1–2):107–114 (1985)) and 6-nitroquipazine (Hashimoto, K., and T. Goromaru, *Biochem. Pharmacol.* 41(11):1679–1682 (1991); Hashimoto K, and T. Goromaru, *Neuropharmacology* 30(2):113–117(1991)) have been used for in vitro and in vivo studies. A reduced level of SERT labeled by these tritiated ligands has been demonstrated in post mortem brain sections of patients with depression (Perry, E. K. et al, Br. *J. Psychiat.* 142:188–192 (1983)), Alzheimer's and Parkinson's diseases (D'Amato, R. et al., *Pharmacol. Exp. Ther.* 242(1):364–371 (1987)) as well as in the frontal cortex of a suicide victim (Mann, J. J., *Nature Medicine* 4(1):25–30 (1998)). The in vitro binding studies suggest that using in vivo imaging methods to evaluate the density of SERT may be clinically important.

Anti-depressive drugs, such as Prozac, operate to inhibit serotonin reuptake by binding with the serotonin transporter (SERT) protein, effectively blocking the binding of the protein with serotonin. Although Prozac has been found to be an effective anti-depressant treatment, it has side effects which can be serious. Prozac is known to bind to the serotonin transporter (SERT) protein, but the responses of patients can differ widely. Some patients experience greater binding than others. If a patient is not responding to Prozac treatment, there is currently no way to determine why that is the case. Frequently, the physician will simply administer greater doses of the drug, a practice which will not necessarily lead to better results and which can enhance undesirable side effects.

Development of selective tracers for positron emission tomography (PET) and single photon emission tomography (SPECT) have made it possible to study in vivo neuroreceptors or site-specific bindings non-invasively in the human brain. However, development of PET or SPECT tracers specifically for in vivo imaging of SERT has only met with limited success. The most promising radioligand described to date is [$^{11}$C](+)McN5652 for PET imaging (Szabo, Z. et al., *Synapse* 20(1):37–43 (1995); Szabo, Z. et at., *J. Nucl. Med.* 37(5):125 (1996); Szabo. Z. *Behav. Brain Res.* 73(1): 221–224 (1995); Szabo, Z. et al, *J. Cerebral Blood Flow & Metabol.* 15(5):798–805 (1995); Suehiro, M. et al., *J. Nucl. Med.* 34(1): 120–127 (1993); Suehiro, M. et al., *Nucl. Med. Biol* 22(4):543–545 (1995)). Specific binding of [$^{11}$C](+) McN5652 correlates well with the known density of SERT sites in the human brain (Szabo, Z. et al., *Synapse* 20(1): 3743 (1995)). In search of a clinically useful SPECT ligand for SERT, several radioiodinated compounds have been evaluated including 4-I-tomoxetine (Kung, M. P. et al., *Life Sci.* 51:95–106 (1992)). Among these tracers only [I$^{23}$I]5-iodo-6-nitroquipazine (Biegon, A. et al., *Brain Res.* 619:236–246 (1993); Mathis, C. A. et at, *Brain Res.* 619:229–235 (1993); Mathis, C. A. et al., *Eur. J. Pharmacol* 210(1):103–104 (1992)) showed promising properties for mapping SERT sites in monkey's brain (Jagust, W. J. et al., *J. Nucl. Med.* 37(7):1207–1214 (1996)). No human study of [$^{123}$I]5-iodo-6-nitroquipazine has been reported. The high nonspecific binding and the fast peripheral metabolism observed with [$^{123}$I]-5 iodo-6-nitroquipazine in non-human primates may limit its application as a clinically useful SPECT imaging agent for SERT in the human brain. Previously, it has been suggested that [$^{123}$I]β-CIT(2β-carbomethoxy-30-(4-iodophenyl)tropane), a SPECT imaging agent, which binds to both DAT and SERT, will be able to clarify pathological changes in both dopaminergic and serotonergic systems. However, overlapping uptake regions and differential kinetics of [$^{123}$I]-CIT binding to DAT and SERT were observed (Fujita, M. et al., *Eur. J. Nucl. Med.* 23(4):431–436 (1996); Kuikka, J. T. et al., *Eur. J. Nucl. Med.* 22(4):346–250 (1995); Tiihonen, J. et al., *Eur. J. Nucl. Med.* 24(10):1253–1260 (1997)). Nonetheless, the effect of a selective SSRI in human brain in vivo has been directly measured by [$^{123}$I]β-CIT/SPECT imaging of SERT sites in depressed patients undergoing treatment with citalopram (Pirker, W. et al.,*J. Neural Trans. Gen Sec.* 100(3):247–256 (1995)). A more selective series of compounds, nor-β-CIT (N-demethylated analog of β-CIT) (Bergstrom, K. A. et al., *Eur. J. Nucl. Med.* 24(6):596–601 (1997)) and related derivatives, (Blough, B. E. et al., *J. Med. Chem.* 40(24): 3861–3864 (1997)) have recently been reported as improved SPECT imaging agents for SERT. It is suggested that [$^{123}$.I]nor-β-CIT might be a suitable alternative tracer for visualization of SERT sites in the human brain with SPECT (Bergstrom, K. A. et al. *Eur. J. Nucl. Med.* 24(6):596–601 (1997); Hiltunen, J. et al., *Eur. J. Nucl. Med.* 25(1): 19–23 (1998)). However, [$^{123}$I]nor-β-CIT still binds to both DAT and SERT, and the selectivity is not sufficient to distinguish between these two motioamline transporter sites. The need for a selective SERT/SPECT imaging agent is still unfulfilled. Therefore, there is a strong impetus to find an improved agent with a better selectivity for imaging SERT in the brain.

A chlorinated compound, 5-chloro-2-((2-((dimethylamino)methyl)phenyl)thio)benzyl alcohol (403U76), was reported as an inhibitor for serotonin uptake and norepinephrine uptake in rat brain synaptosomes ($K_i$=2.1 and 55 nM, respectively) (Ferris, R. M. el at, *J. Pharm. Pharmacol.* 47:775–781 (1995); Brieaddy, L. E., "*Substituted diphenylsulfides as serotonin uptake inhibitors,*" published International Patent Appl. No. WO 93/12080 (1993); Mehta, N. B. et al., "*Halogen substituted diphenylsulfides,*" published European Patent Application EP 402,097 A1 (1990)).

SUMMARY OF THE INVENTION

A first aspect of the present invention is directed to compounds of Formula I:

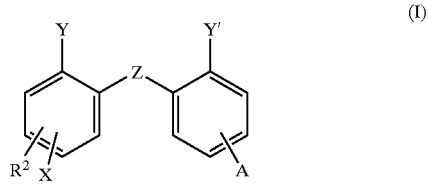

(I)

or a pharmaceutically acceptable salt thereof, wherein

X is hydrogen, Cl, Br, I, $NO_2$, $NR^3R^4$ or —L—Ch;

Y is hydrogen, —$CH_2OR^5$, —$CH_2NCH_3R^1$, $NO_2$, $NR^3R^4$ or —L—Ch;

Y' is hydrogen, —$CH_2OR^5$, —$CH_2NCH_3R^1$, $NO_2$, $NR^3R^4$ or —L—Ch; provided that at least one of the Y or Y' is —$CH_2NCH_3R^1$;

Z is S, O, $NR_6$, $CR^7R^8$, C(O) or —C(=$CR^7R^8$)—;

A is hydrogen, Cl, I, Br or —L—Ch;

$R^1$ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, naphthylmethyl or —L—Ch;

$R^2$ is hydrogen or methyl;

$R^3$ and $R^4$ are independently hydrogen, hydroxy, $C_1$–$C_5$ alkyl, $C_3$–C, cycloalkyl, $C_{1-5}$ alkylcarbonyl, ($C_3$–$C_8$ cycloalkyl)carbonyl, phenyl, benzyl, naphthyl, naphthylmethyl or —L—Ch;

$R^5$ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, naphthylmethyl or —L—Ch;

$R^6$ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, or naphthylmethyl or —L—Ch;

$R^7$ and $R^8$ are independently hydrogen, $C_1$–$C_5$ alkyl or chloro;

L is a covalent bond or a linking group, such as —($CH_2)_n$—, or —$CH_2$), —C(O)—, where n is 1–5;

Ch is a tetradentate ligand capable of chelating a metal;

with the proviso that one and only one of X, Y, A, $R^1$, $R^3$, $R^4$, $R^5$ or $R^6$ is —L—Ch; or with the proviso that X or A is Br or I.

The present invention is further directed to radiolabeled compounds of 3 Formula I wherein X or A is radioactive iodine or radioactive bromine.

The present invention is further directed to radiolabeled compounds (or intermediate thereof) of Formula I wherein one of X, $R^1$, $R^3$, $R^4$, $R^5$ or $R^6$ is —L—Ch.

The present invention is also directed to imaging agents comprising a compound of claim 1 where X is a radioactive bromine or iodine isotope.

The present invention is also directed to imaging agents comprising a compound of claim 1 where one of X, $R^1$, $R^3$, $R^4$, $R^5$ or $R^6$ is —L—Ch, and Ch is one of Formulae V, VI or VII.

BRIEF DESCRIPTION OF THE FIGURES

FIGS. 4A–4F depict ex vivo autoradiographic localization of [$^{125}$I]IDAM binding sites in rats after 60 min post-injection. High levels of radioactivity were observed in the areas containing high densities of serotonin transporter sites. The coronal sections corresponding to a stereotaxic atlas are as follows: 4A: plate 14; 4B: plate 19; 4C: plate 24; 4D: plate 31; 4E: plate 39; 4F: plate 48. CX: cortex; Cpu: caudate putamen; LSD: lateral septum; OT: olfactory tubercle; GP: globus pallidus; ThN: thalamus nuclei; HN: hypothalamic nuclei; CA1, CA2: fields CA1 CA2 Ammon's horn; IP: interpeduncular nucleus; SN: substantia nigra; SC: superior colliculus; DR: dorsal raphe; MR: medial raphe.

DETAILED DESCRIPTION OF THE INVENTION

Figure 1:
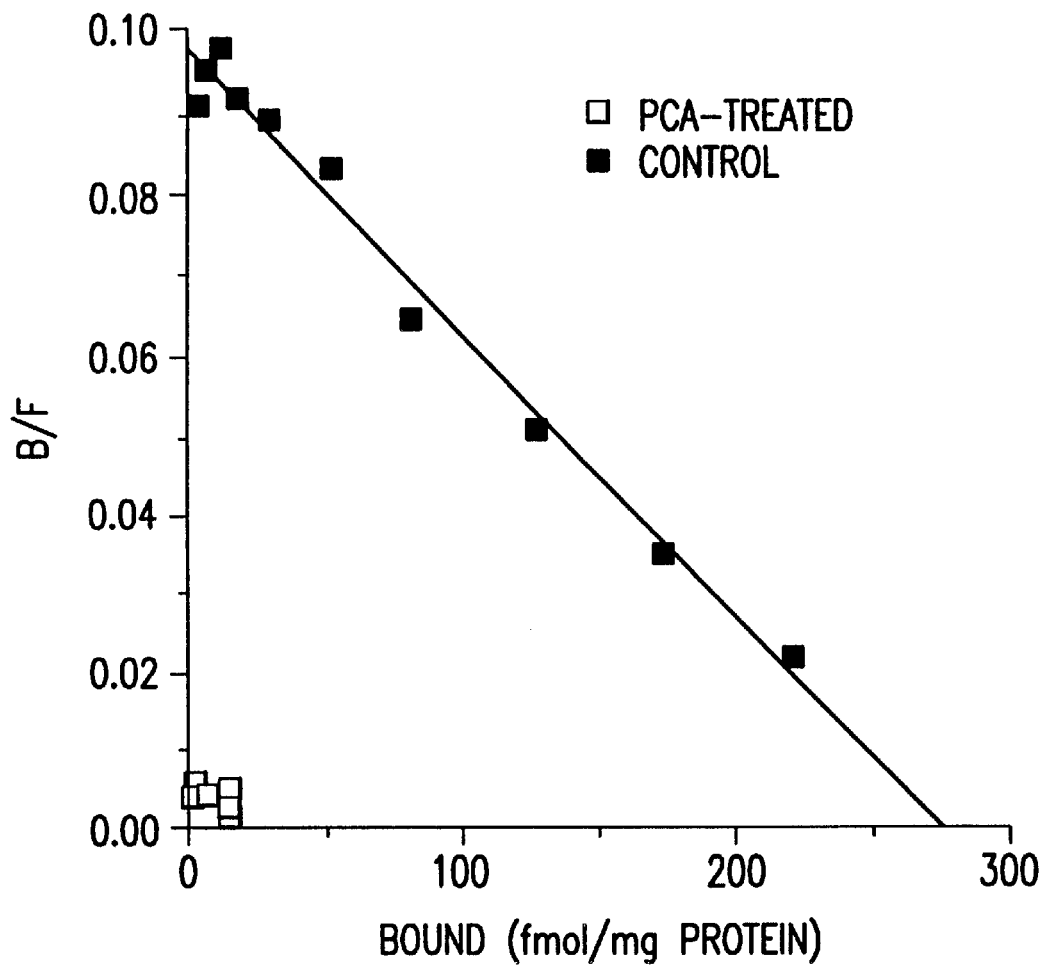
FIG. 1 depicts a Scatchard analysis of [$^{125}$I]IDAM binding to frontal cortical membrand homogenate prepared from saline control and PCA-treated rats. The data are the average values from 4 control and 4 PCA-treated rats (Control: $K_d$=0.25 nM±0.05 nM, $B_{max}$=272±30 fmol/mg protein PCA-lesion:$K_d$=0.050±0.15 nM, $B_{max}$, 20±7 fmol/mg protein).

A first aspect of the present invention is directed to compounds of Formula I:

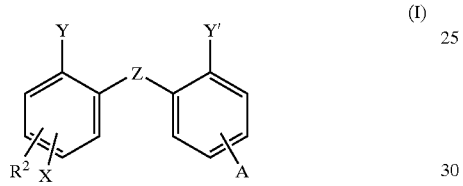
(I)

or a pharmaceutically acceptable salt thereof; wherein

X is hydrogen. Cl, Br, I, NO$_2$, NR$^3$R$^4$ or —L—Ch;

Y is hydrogen, —CH$_2$OR$^5$, —CH$_2$NCH$_3$R$^1$, NO$_2$, NR$^3$R$^4$ or —L—Ch;

Y' is hydrogen, —CH$_2$OR$^5$, CH$_2$NCH$_3$R$^1$, NO$_2$, NR$^3$R$^4$ or —L—Ch;

provided that at least one of the Y or Y' is —CH$_2$NCH$_3$R$^1$;

Z is S, O, NR$^6$, CR$^7$R$^8$, C(O) or —C(—CR$^7$R$^8$)-;

A is hydrogen, Cl, I, Br or —L—Ch;

R$^1$ is hydrogen, C$_1$–C$_5$ alkyl, C$_3$–C$_8$ cycloalkyl, C$_{1-5}$ alkylcarbonyl, (C$_3$–C$_8$ cycloalkyl)carbonyl, phenyl, benzyl, naphthyl, naphthylmethyl or —L—Ch;

R$^2$ is hydrogen or methyl;

R$^3$ and R$^4$ are independently hydrogen, hydroxy, C$_1$→C$_5$ alkyl, C$_3$–C$_8$ cycloalkyl, C$_{1-5}$ alkylcarbonyl, (C$_3$–C$_8$ cycloalkyl)carbonyl, phenyl, benzyl, naphthyl, naphthylmethyl or —L—Ch;

R$^5$ is hydrogen, C$_1$–C$_5$ alkyl, C$_3$–C$_8$ cycloalkyl, C$_{1-5}$ alkylcarbonyl, (C$_3$–C$_8$ cycloalkyl)carbonyl, phenyl, benzyl, naphthyl, naphthylmethyl or —L—Ch;

R$^6$ is hydrogen, C$_1$–C$_5$ alkyl, C$_3$–C$_8$ cycloalkyl, C$_{1-5}$ alkylcarbonyl, (C$_3$–C$_8$ cycloalkyl)carbonyl, phenyl, benzyl, naphthyl, or naphthylmethyl or —L—Ch;

R$^7$ and R$^8$ are independently hydrogen, C$_1$–C$_5$ alkyl or chloro;

L is a covalent bond or a linking group, such as —CH$_2$)$_n$—, or —(CH$_2$)$_n$—C(O)—, where n is 1–5;

Ch is a tetradentate ligand capable of complexing with a metal, such as a ligand selected from the group consisting of:

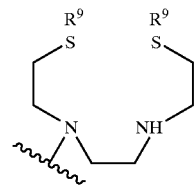
(II)

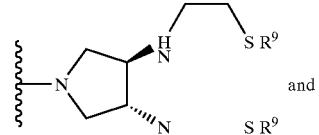
(III)

and

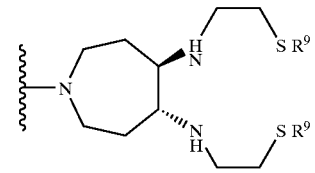
(IV)

with the proviso that one and only one of X, Y, A, R$^1$, R$^3$, R$^4$, R$^5$ or R$^6$ is —L—Ch; or with the proviso that X or A is Br or I.

The present invention is further directed to radiolabeled compounds of Formula I wherein X or A is radioactive iodine or radioactive bromine.

The present invention is further directed to radiolabeled compounds of Formula I wherein one and only one of X, A, R$^1$, R$^3$, R$^4$, R$^5$ or R$^6$ is —L—Ch. In this embodiment, compounds having Ch ligands, such as those of Formulae II, III and IV are complexed with 99m-pertechnetate, as described herein to form metal chelates where Ch is selected from the group consisting of:

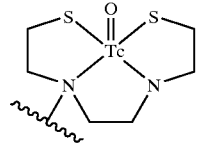
(V)

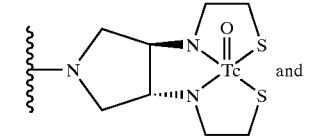
(VI)

and

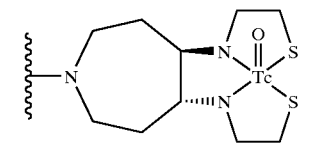
(VII)

In one preferred embodiment, compounds of the invention have the general formula:

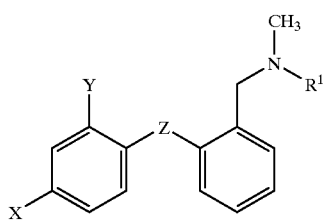

(VIII)

or a pharmaceutically acceptable salt thereof, where X, Y, Z and $R^1$ are as defined for Formula I above.

In another preferred embodiment, compounds of the invention have the general formula:

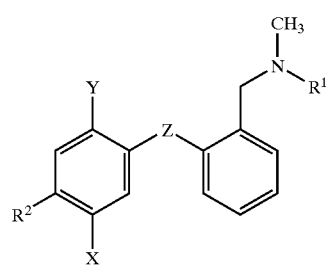

(IX)

or a pharmaceutically acceptable salt thereof, where X, Y, Z and $R^1$ are as defined above for Formula I, and $R^2$ is methyl.

In yet another preferred embodiment, compounds of the invention have the general formula:

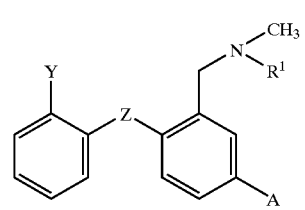

(X)

or a pharmaceutically acceptable salt thereof, where
  A is Br, I or —L—Ch; where L and Ch are as defined above for Formula I;
  Z is O, S, N(CH$_3$), C(O), C(=CH$_2$), or CH$_2$, preferably O, S or CH$_2$; and
  Y and $R^1$ are as defined above for Formula I More preferably, A is $^{123}$I, $^{131}$I, $^{125}$I, $^{77}$Br, or $^{76}$Br; or A is —L—Ch, where Ch is Formula II or Formula V and L is a covalent bond or C$_{1-2}$ alkylene group.

Preferred compounds of Formula VIII include compounds, or pharmaceutically acceptable salts thereof, where
  X is I or Br,
  Y is CH$_2$OH; CH$_2$OCH$_3$; —NHR$^4$, where R$^4$ is hydrogen, hydroxy, or C$_{1-5}$ alkyl; —NO$_2$; or CH$_2$OC(O)CH$_3$;
  Z is S, O, N(CH$_3$), C(O), C(=CH$_2$), or CH$_2$, more preferably S; and
  $R^1$ is methyl.

More preferably X is $^{123}$I, $^{131}$I, $^{125}$I, $^{77}$Br or $^{76}$Br, most preferably $^{123}$I.

Preferred compounds of Formula IX include compounds, or pharmaceutically acceptable salts thereof, where
  X is hydrogen, or I;
  Y is CH$_2$OH, —CH$_2$OCH$_3$, —NH$_2$, or —OH;
  Z is S; and
  $R^1$ is hydrogen or methyl.

More preferably X is $^{123}$I, $^{131}$I, $^{125}$I, $^{77}$Br or $^{76}$Br, most preferably $^{123}$I.

Another aspect of the invention is directed to compounds of the invention where one of X, $R^1$, $R^3$, $R^4$, $R^5$ or $R^6$ is —L—Ch. In this aspect, $R^9$, in each instance, is preferably hydrogen, methoxymethyl, methoxyethoxymethyl, p-methoxybenzyl or benzyl, and the other variable groups have the preferred values mentioned above.

Compounds of the present invention include:

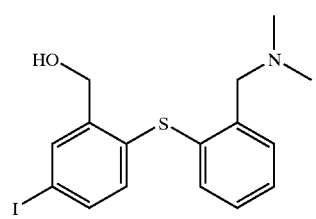

(1)

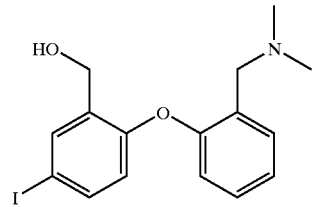

(2)

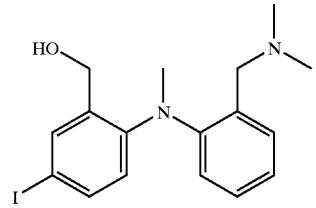

(3)

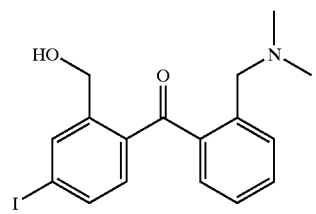

(4)

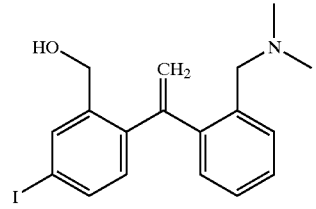

(5)

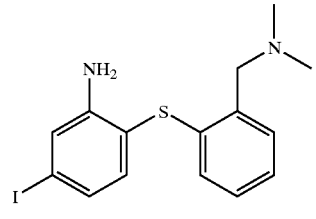

(6)

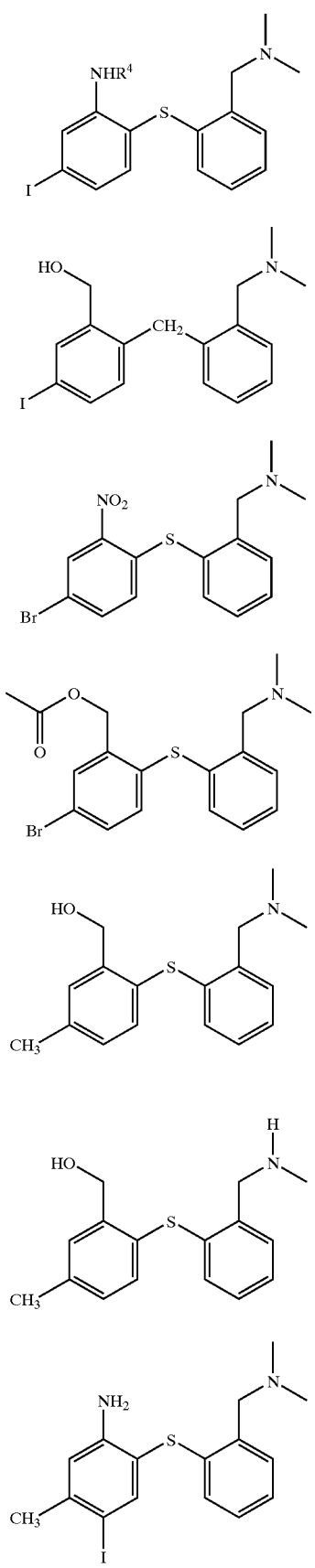
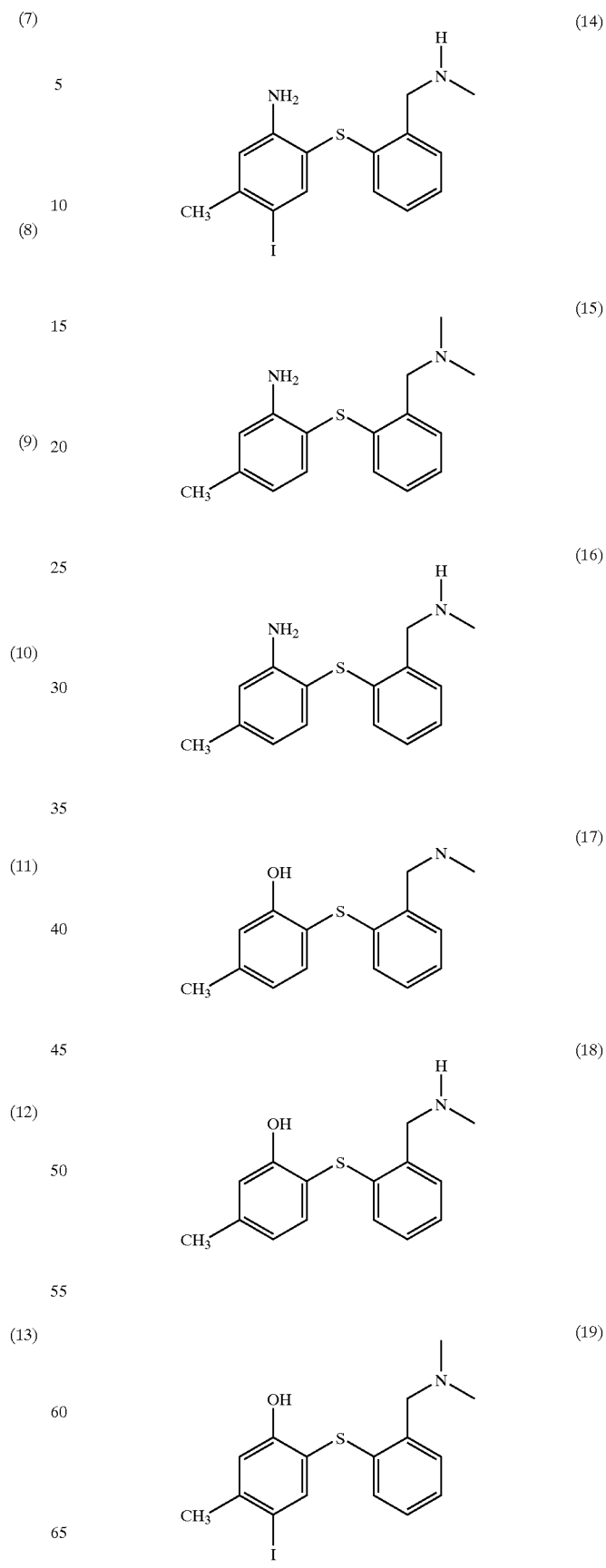

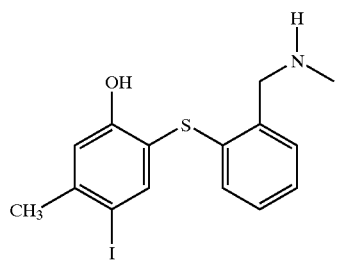

Figure 6:
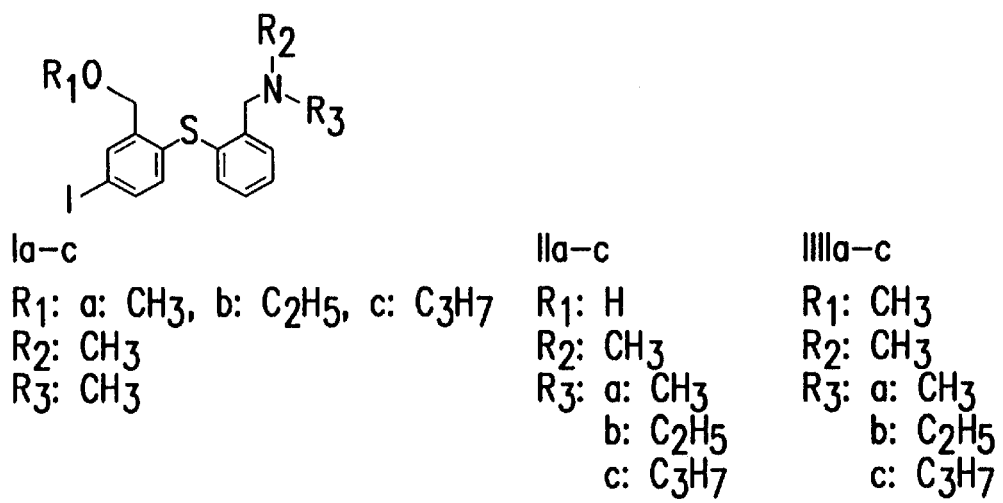
FIG. 6 lists the structures of various compounds that can be synthesized according to the methods described in the application.

(20)

and the compounds listed in Tables 1A and 1B, FIG. 6 and the target compounds of Schemes 9–13;
as well as acid addition salts thereof, where
$R^4$ is defined above; and
each I is preferably $^{123}$I, $^{131}$I, or $^{125}$I, and each Br is preferably $^{77}$Br or $^{76}$Br.

When the compounds of this invention are to be used as imaging agents, they must be labeled with suitable radioactive halogen isotopes. Although $^{125}$I-isotopes are useful for laboratory testing, they will generally not be useful for actual diagnostic purposes because of the relatively long half-life (60 days) and low gamma-emission (30–65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I (half life of 2 hours). Suitable bromine isotopes include $^{77}$Br and $^{76}$Br.

The radiohalogenated compounds of this invention lend themselves easily to formation from materials which could be provided to users in kits. Kits for forming the imaging agents can contain, for example, a vial containing a physiologically suitable solution of an intermediate of Formula I in a concentration and at a pH suitable for optimal complexing conditions. The user would add to the vial an appropriate quantity of the radioisotope, e.g., Na$^{123}$I, an oxidant, such as hydrogen peroxide. The resulting labeled ligand may then be administered intravenously to a patient, and receptors in the brain imaged by means of measuring the gamma ray or photo emissions therefrom.

Pharmaceutically-acceptable salts of the compounds of this invention include the acid addition salts derived from non-toxic inorganic acids such as hydrochloric acid, nitric acid, phosphoric acid, sulfuric acid, hydrobromic acid, hydroiodic acid, phosphorous acid and the like. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids.

Examples of useful organic acids are carboxylic acids such as maleic acid, acetic acid, tartaric acid, propionic acid, fumaric acid, isethionic acid, succinic acid, cyclamic acid, pivalic acid and the like; useful inorganic acids are hydrohalide acids such as HCl, HBr, HI; sulfuric acid; phosphoric acid and the like. Preferred acids for forming acid addition salts include HCl and acetic acid.

The term "alkyl" as employed herein by itself or as part of another group refers to both straight and branched chain radicals of up to 8 carbons, such as methyl, ethyl, propyl, isopropyl, butyl, t-butyl, isobutyl, pentyl, hexyl, isohexyl, heptyl, and octyl.

In embodiments where one of X, $R^1$, $R^3$, $R^4$, $R^5$ or $R^6$ is —L—Ch, the groups $R^9$ are both hydrogen, or can be any of the variety of protecting groups available for sulfur, including methoxymethyl, methoxyethoxymethyl, p-methoxybenzyl or benzyl. Sulfur protecting groups are described in detail in Greene, T. W. and Wuts, P. G. M., *Protective Groups in Organic Synthesis,* 2nd Edition, John Wiley and Sons. Inc., New York (1991). Protecting group $P^a$ can be removed by appropriate methods well known in the art of organic synthesis, such as trifluoroacetic acid, mercuric chloride or sodium in liquid ammonia. In the case of Lewis acid labile groups, including acetamidomethyl and benzamidomethyl, $R^9$ can be left intact. Labeling of the ligand with technetium in this case will cleave the protecting group, rendering the protected diaminedithiol equivalent to the unprotected form.

Tc-99m complexes are prepared as follows. A small amount of non-radiolabeled compound (1–2 mg) is dissolved in 100 μL EtOH and mixed with 200 μL HCl (1 N) and 1 mL Sn-glucoheptonate solution (containing 8–32 μg SnCl$_2$ and 80–320 μg Na-glucoheptonate, pH 6.67) and 50 μL EDTA solution (0.1 N). [$^{99m}$Tc]Pertechnetate (100–200 μL; ranging from 2–20 mCi) saline solution are then added. The reaction is heated for 30 min at 1000° C., then cooled to room temperature. The reaction mixture is analyzed on TLC (EtOH:conc. NH$_3$ 9:1) for product form ation and purity check. The mixture can be neutralized with phosphate buffer to pH 5.0.

The radioactive diagnostic agent should have sufficient radioactivity and radioactivity concentration which can assure reliable diagnosis. For instance, in case of the radioactive metal being technetium-99m, it may be included usually in an amount of 0.1 to 50 mCi in about 0.5 to 5.0 ml at the time of administration. The amount of a compound of Formula I may be such as sufficient to form a stable chelate compound with the radioactive metal.

The thus formed chelate compound as a radioactive diagnostic agent is sufficiently stable, and therefore it may be immediately administered as such or stored until its use. When desired, the radioactive diagnostic agent may contain any additive such as pH controlling agents (e.g., acids, bases, buffers), stabilizers (e.g., ascorbic acid) or isotonizing agents (e.g., sodium chloride).

The present invention further relates to a method of preparing a technetium-99m complex according to the present invention by reacting technetium-99m in the form of a pertechnetate in the presence of a reducing agent and optionally a suitable chelator with an appropriate Ch-containing compound.

The reducing agent serves to reduce the Tc-99m pertechnetate which is eluted from a molybdenum-technetium generator in a physiological saline solution. Suitable reducing agents are, for example, dithionite, formamidine sulphinic acid, diaminoethane disulphinate or suitable metallic reducing agents such as Sn(II), Fe(II), Cu(I), Ti(III) or Sb(III). Sn(II) has proven to be particularly suitable.

For the above-mentioned complex-forming reaction, technetium-99m is reacted with an appropriate compound of the invention as a salt or in the form of technetium bound to comparatively weak chelators. In the latter case the desired technetium-99m complex is formed by ligand exchange. Examples of suitable chelators for the radionuclide are dicarboxylic acids, such as oxalic acid, malonic acid, succinic acid, maleic acid, orthophtalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because a chelate of technetium-99m with one of these chelators undergoes the desired ligand exchange particularly easily.

The most commonly used procedure for preparing [Tc$^v$O]$^{+3}$N$_2$S$_2$ complexes is based on stannous (II) chloride reduction of [$^{99m}$Tc]pertechnetate, the common starting material. The labeling procedure normally relies on a Tc-99m ligand exchange reaction between Tc-99m (Sn)-glucoheptonate and the N$_2$S, ligand. Preparation of stannous (II) chloride and preserving it in a consistent stannous (II) form is critically important for the success of the labeling reaction. To stabilize the air-sensitive stannous ion it is a common practice in nuclear medicine to use a lyophilized kit, in which the stannous ion is in a lyophilized powder form mixed with an excess amount of glucoheptonate under an inert gas like nitrogen or argon. The preparation of the lyophilized stannous chloride/sodium glucoheptonate kits ensures that the labeling reaction is reproducible and predictable. The N$_2$S$_2$ ligands are usually air-sensitive (thiols are easily oxidized by air) and there are subsequent reactions which lead to decomposition of the ligands. The most convenient and predictable method to preserve the ligands is to produce lyophilized kits containing 100–500 μg of the ligands under argon or nitrogen.

Since the radiopharmaceutical composition according to the present invention can be prepared easily and simply, the preparation can be carried out readily by the user. Therefore, the present invention also relates to a kit, comprising:

(1) A non-radiolabeled compound of the invention, the compound optionally being in a dry condition; and also optionally having an inert, pharmaceutically acceptable carrier and/or auxiliary substances added thereto; and (2) a reducing agent and optionally a chelator; wherein ingredients (1) and (2) may optionally be combined; and further wherein instructions for use with a prescription for carrying out the above-described method by reacting ingredients (1) and (2) with technetium-99m in the form of a pertechnetate solution may be optionally included.

Examples of suitable reducing agents and chelators for the above kit have been listed above. The pertechnetate solution can be obtained by the user from a molybdenum-technetium generator. Such generators are available in a number of institutions that perform radiodiagnostic procedures. As noted above the ingredients (1) and (2) may be combined, provided they are compatible. Such a monocomponent kit, in which the combined ingredients are preferably lyophilized, is excellently suitable to be reacted by the user with the pertechnetate solution in a simple manner.

Methods of Making

Diphenylsulfide compounds of the present invention can be synthesized using methods analogous to those described in Ferris, R. M. et al., *J. Pharm. Pharmacol.* 47:775–781 (1995); Brieaddy, L. E., "*Substituted diphenylsulfides as serotonin uptake inhibitors*," published International Patent Appl. No. WO 93/12080 (1993); and Mehta, N. B. et al. "*Halogen substituted diphenylsulfides*," published European Patent Application EP 402,097 A1 (1990).

Additionally, compounds of the invention can be formed by the following methods, illustrated in the schemes appearing at the end of the detailed description.

Scheme 1 depicts a synthetic method for forming IDAM.

Scheme 2 depicts a synthetic method for forming compounds of the invention where Y is —CH$_2$ OR$^5$ and R$^5$ is various lower alkyl groups.

Scheme 3 depicts a synthetic method for forming compounds of the invention where R$^1$ can be various lower alkyl groups.

Scheme 4 depicts a synthetic method for preparing compounds of the invention where Z is oxygen, such as ODAM.

Schemes 5 and 6 depict synthetic routes for preparing compounds of the invention where Y is —NR$^3$ R$^4$.

Scheme 7 depicts a synthetic route for preparing compounds of the invention where Y is —L—Ch, where L is a bond and Ch is Formula II.

Scheme 8 depicts synthetic steps for preparing compounds having various groups at the R$^1$ position.

Schemes 9, 10 and 11 depict a synthetic method for forming compounds of the invention where Z is —CH$_2$—, A is iodo and Y is hydrogen, dimethylaminomethyl or hydroxymethyl, such as CARDAM1, CARDAM2 and CARDAM5X.

Scheme 12 depicts a synthetic method for forming compounds of the invention where Z is NH, and one of A or X is iodo.

Scheme 13 depicts a synthetic method for preparing compounds of the invention where X is —L—Ch, where L is a bond and Ch is Formula II or V.

Experimental Proton NMR spectra were run on a Brukker 200 spectrometers. The chemical shifts (δ) were reported in ppm downfield from the tetramethylsilane standard; CDCl$_3$ or CD$_3$OD was used as the solvent. Mass spectra were carried out at Department of Chemistry, University of Pennsylvania

EXAMPLE 1

5-iodo-2-[[2-2[(dimethylamino)methyl]phenyl]thio] benzyl alcohol (IDAM) and (5-bromo-2-[[2-2 [(dimethylamino)methyl]phenyl]thio]benzyl alcohol)

The synthesis of 5-iodo-2-[[2-2[(dimethylamino)-methyl] phenyl]thio]benzyl alcohol (IDAM) and its bromo derivative (5-bromo-2-[[2-2[(dimethylamino)methyl]phenyl]thio] benzyl alcohol) was achieved by a reaction sequence outlined in Scheme 1 shown on page 37 of this application. The direct coupling of 2,5-dibromobenzoic acid (Frazer, A., *J. Clin. Psychiatry.* 6:9–25 (1997)) or 2,5-diiodobenzoic acid (Mathis, C. A. et al., *J. Nucl. Med.* 33:890(1992)) with 2-thio-N,N-dimethylbenzamide (Wong, D. T. et al. *Adv. Exp. Med. & Biol.,* 363:77–95 (1995)) was carried out in N,N-dimethylacetamide (DMAC) with sodium methoxide to give the desired compounds in good yield (59 and 44% for 23 and 28, respectively). Only when 2-thio-N,N-dimethylbenzamide was freshly prepared, was a good coupling yield achieved. This may due to the fact that the free thiol of 22 was not stable upon prolonged standing at room temperature. The bromo compound was converted to the corresponding tri-n-butyltin derivative (Maryanoff. E. M. et al., *J. Med. Chem.* 33:2793–2797 (1990)) by a tetrakis (triphyenlphosphine)palladium(0)-catalyzed reaction with good yield (66%). The tin derivative was successfully converted to IDAM with excellent yield (97%), or alternatively, 2-((4-iodo-2-carboxyphenyl)thio)N,N-dimethylbenzamide (Mathis, C. A. et al., *Eur. J. Pharmacol.* 210:103–104 (1992)) was reduced to IDAM with 66% yield.

EXAMPLE 2

Radioiodination of 5-iodo-2-[[2-2-[(dimethylamino) methyl]phenyl]thio]benzyl alcohol Radioiodination was carried out by an iododestannylation reaction (Maryanoff, E. M. et al., *J. Med. Chem.* 33:2793–2797 (1990)). IDAM was treated with bistributyl-tin and Pd(PPh$_3$)$_4$ (see Example 4, Step (1)). The stannylated intermediate was reacted with radioactive sodium iodide (I-125 or I-123) in the presence of hydrogen peroxide. The final [$^{125}$I or $^{123}$I]IDAM was purified using HPLC method (purity>99%, Rt=11.38 min, PRP-1 column eluted, 1 mL/min, with a 80:20 mixture of acetonitrile and 3,3-dimethylglutaric acid buffer, pH 7.4).

The radioiodinated ligand, [$^{125}$I]or [$^{123}$I]IDAM (26, Scheme 1), was successfully prepared from the corresponding tributyltin derivative by an iododestannylation reaction, which resulted in a nocarrier-added tracer (specific activity is comparable to that of Na$^{125}$I; or Na$^{123}$I). The radiochemical identity of the radioiodinated ligand was verified by a co-injection of the nonradioactive compound, IDAM, which showed an identical retention time of 7 min on HPLC profiles. [$^{125}$I]IDAM has been shown to be stable in 50% ethanol for up to two months after radioiodination (>95% radiochemical purity determined by HPLC). [$^{123}$I]IDAM displayed excellent in vitro stability with no decomposition observed upon prolonged standing (>20 hr) at 0–4° C. in saline solution.

EXAMPLE 3

5-Iodo-2-(2-dimethylaminomethylphenoxy)Benzyl Alcohol

Methyl, 5-nitro-2-(2-methylphenoxy)benzoic acid (34) To a solution of 2-chloro-5-nitro benzoic acid 31 (4.04 g, 20 mmol) in nitrobenzene (20 mL) was added $K_2CO_3$ (4.14 g, 3 eq) followed by Cu (0.2 g) and CuI (0.2 g) at 70–80° C. The mixture was stirred at 80° C. for 10 min. O-Cresol (4.32 g, 2 eq) was added and the mixture was stirred at 155° C. overnight. NaOH solution (1M, 30 mL) was added after the mixture was cooled down and the dark slurry was extracted with ether to remove nitrobenzene. The aqueous phase was filtered and acidified with HCl. The resulting mixture was extracted with mixed solvent ($CH_2Cl_2$:MeOH=9:1). The organic phase was dried, filtered and concentrated to give a tar (4.6 g). To the solution of tar obtained above in MeOH (100 mL) was added concentrated $H_2SO_4$ (2 mL) dropwise at room temperature and the mixture was stirred under reflux overnight. Solvent was removed and ice water was added. The mixture was made basic with KOH solution and extracted with $CH_2Cl_2$. The organic phase was dried, filtered and concentrated to give crude product which was purified by chromatography (Flash 40) (EtOAc:Hex=1:10) to give 720 mg of product and 2.5 g of mixture (product and by product). $^1$H NMR (CDCl$_3$, δ): 2.19 (s, 3H, ArCH$_2$), 3.96 (s, 3H, COOCH$_3$), 6.73 (d, 1H, J=9.2 Hz, ArH), 7.00 (d,d, 1H, J=7.4, 1.8 Hz, ArH), 7.15–7.34 (m, 3H, ArH), 8.23 (d,d, 1H, J=7.5, 1.8 Hz, ArH), 8.79 (d, 1H, J=2.8 Hz, ArH).

Methyl, 5-nitro-2-(2-bromomethylphenoxy)-benzoic acid (35) To a solution of starting material 34 (720 mg, 2.5 mmol) in CCl$_4$ (20 mL) was added NBS (491 mg, 1 eq) and AIBN (40 mg, 0.24 mmol). The mixture was stirred under reflux overnight. The cool solution was filtered and the solvent was removed to give an oil which was purified by chromatography (Flash 40) (EtOAc:Hex=1:10) to give 130 mg of product and 710 mg of mixture (product and byproduct). $^1$H NMR (CDCl$_3$, δ): 3.94 (s, 3H, COOCH$_3$), 4.56 (s, 2H, NCH$_2$), 6.95 (d, 2H, J=9.1 Hz, ArH), 7.24 (t,d, 1H, J=7.4, 1.1 Hz, ArH), 7.36 (t, d, 1H, 1=7.6, 1.7 Hz, ArH), 7.52 (d,d, 1H J=7.4, 1.1 Hz. ArH, 8.25 (d,d, 1H, J=9.2, 2.8 Hz, ArH, 8.81 (d, 1H, J=2.8, 1.1 Hz, ArH).

Methyl, 5-nitro-2-(2-dimethylaminomethylphenoxy)-benzoic acid (36) To a solution of starting material 35 (300 mg, 0.82 mmol) in acetonitrile (10 mL) was added diemthylamine (5 mL, 2M in THF) and triethylamine (1 mL) dropwise at room temperature. The mixture was stirred under reflux overnight. Solvent was removed and the residue was purified by preparative thin layer chromatography (PTLC) (CH$_2$Cl$_2$:MeOH=9:1) to give 148 mg of product. $^1$H NMR (CDCl$_3$, δ): 2.15 (s, 6H, NCH$_3$), 3.39 (s, 2H, NCH$_2$), 3.92 (s, 3H, COOCH$_3$), 6.73 (d, 1H, J=9.2 Hz, ArH, 6.97 (d, 1H, l=7.5 Hz, Are, 7.24 (t,d, 1H, J=7.0, 1.1 Hz, ArH), 7.30 (t,d, 1H, J=7.3, 1.7 Hz, ArH), 7.52 (d, 1H, J=7.5 Hz, ArH), 8.16 (d,d,d, 1H, J=9.2, 2.8, 1.1 Hz, ArH), 8.75 (d,d, 1H, J=2.8, 1.0 Hz, ArH), HRMS Calcd($C_{17}H_{18}N_2O_5$): M/Z331.1294 (M$^+$1); Found: M/Z331.1301 (M$^+$+1).

Methyl, 5-amino-2-(2-dimethylaminomethylphenoxy) benzoic acid (37) A mixture of starting material 36 (225 mg, 0.68 mmol) and Pd/C (50 mg) in mixed solvent (30 mL, MeOH:EtOAc-1:9) was hydrogenated at 50 psi and room temperature for 2 h. The mixture was filtered and the filtrate was concentrated to give crude product which was purified by PTLC (Ch$_2$Cl$_2$:MeOH=9:1) to give 220 mg of product. $^1$H NMR (CDCL$_3$, δ): 2.67 (s, 6H, NCH$_3$), 3.70 (s, 3H, COOCH$_3$), 4.15 (s, 2H, NCH$_2$), 6.59 (d, 1H, J=8.1 Hz, ArH), 6.84 (d, 2H, J=1.6 Hz, ArH), 7.04 (t, 1H, J=7.4 Hz, ArH), 7.17 (d,d 1H, J+7.7, 1.6 Hz ArH), 7.24 (t, 1H, J=1.1 Hz, ArH), 7.64 (d,d, 1H, J=7.4, 1.5 Hz, ArH). HRMS Calcd ($C_{17}H_{20}N_2O_3$): M/Z301.1552 M$^{++}$1); Found: M/Z301.1549 (M$^+$+1).

5-Amino-2-(2-dimethylaminomethylphenoxy)benzyl alcohol (38) To a suspension of LAH (240 mg, 6.3 mmol) in THF (20 mL) was added dropwise a solution of starting material 37 (410 mg, 1.4 mmol) at room temperature. The mixture was stirred at room temperature for 1 h. 0.2 mL of water, 0.2 mL of NaOH solution (1M and 0.6 mL of water were added dropwise successively to quench the reaction. The mixture was filtered and washed with mixed solvent (CH$_2$Cl$_2$:MeOH=9:1). The filtrate was concentrated and the residue was purified by PTLC (CH$_2$Cl$_2$:MeOH:NH$_4$OH= 9:1:0.1) to give 280 mg of product $^1$H NMR (CD$_3$OD, δ): 2.26 (s, 6H, NCH$_3$), 3.58 (s, 2H, NCH$_2$), 4.33 (s, 2H, HOCH$_2$), 6.58 (d,d, 1H, J+8.1, 1.0 Hz, ArH), 6.67 (d,d, 1H, J+8.5, 2.6 Hz, ArH), 6.74 (d, 1H, J=8.4 Hz, ArH), 6.82 (d, 1H, J=2.5 Hz, ArH), 6.96 (t,d, 1H, J=7.4, 1.2 Hz, ArH), 7.14 (t,d, 1H, J=8.0, 1.8 Hz, ArH, 7.29 (d,d, 1H, J=7.4, 1.7 Hz, ArH), HRMS Calcd($C_{16}H_{20}N_2O_2$): M/Z 273.1603 (M$^+$+1); Found: M/Z 273.1603 (M$^+$+1).

5-Iodo-2-(2-dimethylaminomethylphenoxy)-benzyl alcohol (39) To a mixture of starting material 38 (250 mg, 0.92 mmol), ice (3.6 g) and concetrated HCl (2.4 mL) was added a solution of NaNO$_2$ 9360 mg) in water (4.5 mL) dropwise at 0° C. in an ice bath. The mixture was stirred at 0° C. for 30 min. The resulting mixture was added into a solution of KI (2.1 g) in water (15 mL) dropwise at 0° C. and the resulting mixture was stirred at room temperature for 30 min The mixture was made basic with saturated NaHCO$_3$ solution and extracted with mixed solvent (CH$_2$CL$_2$:MeOH= 9.1). The organic phase was dried, filtered and concentrated to give crude product which was purified by PTLC (CH$_2$Cl$_2$:MeOH=9:1) to give 108 mg of product $^1$H NMR (CDCl$_3$, δ): 2.25 (s, 6H, NCH$_3$), 3.49 (s, 2H, NCH$_2$), 4.29 (s, 2H, HOCH$_2$), 6.67 (d, 1H, J=8.0 Hz, ArH), 6.77 (d, 1H, J=8.2 Hz, Are, 7.02 (t, 1H, J=7.5 Hz, ArH), 7.19 (d,d, 1H, J=7.9, 1.2 Hz, ArH), 7.24 (d, 1H, J=7.2 Hz, ArH), 7.59 (d,d, 1H, J=8.4, 1.7 Hz, ArH), 7.63 (s, 1H, ArH), HRMS Calcd ($C_{16}H_{18}NO_2$): M/Z 384.0461 (M$^+$+1); Found M/Z 384.0472 (M$^+$+1).

EXAMPLE 4

Radioiodination of ODAM 5-tributylstannyl-2-2-dimethylaminomethylphenoxy)-benzyl alcohol (40) A mixture of starting material 39 (30 mg, 0.08 mmol), bistributyltin (0.2 mL) and Pd(PPh$_3$)$_4$ (10 mg) in mixed solvent (2 mL, Et$_3$N:dioxane=1:1) was stirred at 90° C. overnight. Solvent was removed and the residue was purified by PTLC (CH$_2$Cl$_2$:MeOH=9:1) to give 12 mg of product. $^1$H NMR (CDCl$_3$, δ): 0.85–1.69 (m, 27H. SnBu$_3$), 2.25 (s, 6H, NCH$_3$), 3.50 (s, 214, NCH$_2$), 4.35 (s, 2H, HOCH$_2$), 6.69 (d, 1H, J=8.1 Hz, ArH), 6.96 (d, 1H, J=7.8 Hz, ArH), 7.00 (d, 1H, J=8.4 Hz, ArH), 7.17 (d,d, 1H, J=7.7, 1.8 Hz, ArH), 7.22 (d,d, 1H, J=7.2, 1.5 Hz, ArH), 7.37 (s, 1H, ArH), 7.39 (d,d, 1H, J=7.5, 1.2 Hz, ArH), HRMS Calcd(C$_{28}$H$_{45}$NO$_2$Sn): M/Z 548.2550 (M$^+$+I); Found M/Z 548.2548 (M$^+$+1).

5-[123-Iodo or 125-iodo]-2-(2-dimethylaminomethyl-phenoxy)-benzyl alcohol Radioiodination was carried out by iododestannylation. ODAM was reacted with radioactive sodium iodide (I-125 or I-123) in the presence of hydrogen peroxide, and purified by HPLC.

EXAMPLE 5

Biological Activity of Compounds of the Invention

General

Male Spague-Dawley rats weighing 225–275 g were used in this study. No carrier added [$^{125}$I]/[$^{123}$I]NaI (0.1 N NaOH solution) were purchased from Nordion (Ottawa, Canada) and DuPont NEN Research Products (Boston, Mass.), respectively. [$^{125}$I]IPT was prepared according to the procedure described previously (Kung, M. P. et al., *Synapse* 20(4):316–324 (1995)). Paroxetine was generously provided by Di. C. Mathis of University of Pittsburgh. (+)McN5652 was kindly provided by Research Biochemicals Int. through a synthesis program supported by NIMH. Nisoxetine was prepared in our laboratory according to a method reported previously (Srebnik, M. et al. *J. Med. Chem.* 53:2916–2920 (1988)). Serotonin, methylphenidate and raclopride were purchased from Research Biochemicals Int. (Natick, Mass.). Desipramine and p-chloramphetamine (PCA) were purchased from Sigma Chemical Co. (St. Louis, Mo.). All other chemicals used were of reagent grade.

Methods

In Vitro Binding

Cell Lines

Three monoamine transporters expressed respectively in a common parental cell line, LLC-PK, (referred to as LLC-DAT. LLC-NET and LLC-SERT) were kindly provided by Dr. G. Rudnick of Yale University. Cells were plated and grown to confluence as a monolayer as described (Gu, H. et al., *J. Biol. Chem.* 269(10):7124–1130 (1994)). The membrane homogenates were prepared as for for the binding assays with [$^{125}$I]IPT. Inhibition of compounds on [$^{125}$I]IPT binding to LLC-DAT, LLC-NET and LLC-SERT were carried out in the assay buffer (50 mM Tris-HCl, pH 7.4, 120 mM NaCl and 0.1% BSA) containing 0.2–0.4 nM [$^{125}$I]IPT as described previously (Hou, C. et al., *Society for Neuroscience Program 28th Annual Meeting*, Los Angeles, Calif. [abstract 241.21]:112 (1998)). Under these conditions, IPT showed K, values of 1.2, 19.3 and 1.2 nM for DAT, NET and SERT, respectively.

Native Tissues

The frontal cortex of rat brain were dissected and homogenized in 30 volumes of buffer (50 mM Tris-HCl, pH 7.4 containing 120 mM NaCl and 5 mM KCl). The homogenates were centrifuged at 20,000 g for 20 min. The resulting pellets were then re-suspended and recentrifuged. The final pellets were suspended in the same buffer and used for in vitro binding assays.

Binding assays were performed in glass tubes (12×75 mm) with a final volume of 0.5 ml. In saturation experiments, aliquots (100 μl corresponding to 20–30 μg of protein) of membrane suspensions were mixed with buffer (as above) containing 0.05–2.0 nM [$^{125}$I]IDAM.

Competition experiments were performed using 0.2 nM [$^{125}$I]IDAM and 8–10 concentrations ($10^{10}$–$10^{-5}$M) of competing drugs. Various inhibitors were serially diluted with the buffer containing 0.1% BSA to overcome the stickiness and loss due to dilution. Nonspecific binding was defined with 1 μM paroxetine. Incubation was carried out for 60 min at room temperature and then terminated by separation of bound from free radioligand by filtration through glass fiber filters (Schleicher & Schuell No. 25, Keene, N.H.) pre-soaked with 1% polyethylenimine. The filters were then washed three times with 3 ml of ice-cold 20 nM Tris buffer and counted in a gamma counter (Packard 5000) with 70% efficiency. To study the effect of $N^{n+}$, the homogenates were prepared in a sodium-free 50 mM Tris-HCl/5 mM KCl buffer. Final $Na^{n+}$ concentrations of 0, 2, 5, 10, 20, 37.5, 75, 150 and 300 mM were utilized and the same assays were performed as described above. Protein determinations were performed with Lowry's method (Lowry, O. H, et al., *J. Biol. Chem.* 193:265–275 (1951)) using bovine serum albumin as a standard. The results of saturation and competition experiments were subjected to nonlinear regression analysis using EBDA(Munson, P. J. and D. Rodbard, *Anal. Biochem.* 107(7:220–239 (1980)) by which to obtain $K_d$, $B_{max}$ and $IC_{50}$ values.

p-Chloroamphetamine (PCA) Lesion Studies

A neurotoxin, p-chloroamphetamine (PCA), was used to lesion the serotonergic nerve terminals of rats as described previously (Sanders-Bush, E. and V. J. Massari, *Fed Proc.* 36:2149–2153 (1977)). Ten rats were divided into two-groups, and they were injected daily with PCA (8 mg/kg, i.p.) or saline for 3 consecutive days, respectively. The animals were sacrificed 5 days after the last injection and the frontal cortical membrane homogenates were prepared. The difference in the binding sites ($B_{max}$) and affinities ($K_d$) for [$^{125}$I]IDAM were measured between control and PCA-lesioned rats.

Statistics

Effects of drugs on the radioactivity in the various regions of CNS were examined using analysis of variance procedures. IDAM binding in drug-treated rats was compared against control animals in different brain regions, using one-tailed t-tests. The level of significance was defined as $p<0.05$, after Bonferroni correction for multiple comparisons.

Biodistribution in Rats

Three or four rats per group were used for each biodistribution study. While under ether anesthesia, 0.2 ml of a saline solution containing 10 μCi of radioactive tracer was injected into the femoral vein. The rats were sacrificed at the time indicated by cardiac excision while under ether anesthesia. Organs of interest were removed and weighed, and the radioactivity was counted using a Packard automatic gamma counter (Model 5000). The percent dose per organ was calculated by a comparison of the tissue counts to counts of 1% of the initial dose (100 times diluted aliquots of the injected material) measured at the same time.

Regional brain distribution in rats was measured after an i.v. injection of the radioactive tracer. Samples from different brain regions [cortex (CX), striatum (ST), hippocampus (HP), cerebellum (CB) and hypothalamus (HY)] were dissected, weighed and counted. The percentage dose/g of each sample was calculated by comparing sample counts with the counts of the diluted initial dose described above. The ratio of specific binding (SB) in each region was obtained by dividing the difference of each region from the cerebellum (percentage dose/g) with that of the cerebellum [(region-CB)/CB]. The cerebellum region containing no serotonin transporters was used as a background region.

In vivo competitive binding of various uptake of [$^{125}$I] IDAM was investigated by pretreating the animals respectively with paroxetine, (+)McN5652, desipramine, nisoxetine, methylphenidate, raclopride and IDAM (2 mg/kg, each, i.v. at 5 min prior to the injection of [$^{125}$I] IDAM). Experiments were performed using groups of 3–4 animals per study. Similar regional brain distributions were determined at 60 min after [$^{125}$I]IDAM injection as described above. The reduction of regional specific binding in the drug-pretreated rats was compared to the control animals with saline pretreatment.

Metabolite Analysis of Brain Tissue

Sixty minutes after an i.v. injection of 200–300 $\mu$Ci of [$^{125}$I]IDAM into two male rats, the areas corresponding to the hypothalamus region were dissected individually. The tissues were then homogenized in 1.5 ml of 50 mM Tris buffer (pH 7.4) and the homogenates were extracted with ethyl acetate (3×1.5 ml) in the presence of the non-radioactive IDAM (100 $\mu$g). The extracted ethyl acetate layers were evaporated to near dryness and the purity of [$^{125}$I]IDAM in the condensed extracts was analyzed by HPLC (PRP-1 column; solvent: CH$_3$CN/DMGA: 90/10; flow rate: 1 ml/min). Control samples were performed by adding 5–10 $\mu$Ci of [$^{125}$I]IDAM to hypothalamus tissues followed by the same procedures used for the experimental samples to determine the extraction efficiency.

Ex Vivo Autoradiography of [$^{125}$I]IDAM in Rat Brain

Rats under ether anesthesia were injected intravenously with 0.4 ml of a saline solution containing 500 $\mu$Ci of [$^{125}$I]IDAM. At 60 min post i.v. injection, the animals were sacrificed by cardiac excision while under ether anesthesia. The brains were rapidly removed, placed in embedding medium (Tissue Tek, Miles Laboratory, Elkhart, Ind.) and frozen with powdered dry ice. After reaching equilibrium at −20° C. consecutive 20 $\mu$m coronal sections were cut on a cryostat microtome (Hacker Instruments, Fairfield, N.J.) thaw-mounted on microscope slides, and air-dried at room temperature. The slides containing the brain sections were exposed to DuPont x-ray film along with 20 $\mu$m thick $^{125}$I standards (Amersham Corp., Arlington, Ill.) for 72 hr in 9 autoradiographic cassetts. The microscale standards were calibrated with tissue mash standards for the value conversion to nCi/mg protein. The exposed film was developed by a Kodak automatic film processor. The optical densities were determined with an image analysis system developed by NIH (Image 1.61). The blocking studies were carried out by pretreating the rats with paroxetine or nisoxetine (2 mg/kg, i.v. 5 min prior to tracer injection). The brain sections of the pretreated rats were processed following the same procedures described above for the normal untreated rats.

Results

Selectivity for Monoamine Transporters (DAT, SERT and NET)

The binding selectivity for three monoamine transporters of IDAM, ODAM, other compounds of the invention and previously described compounds were compared. The results are reported in Tables 1A and 1B, below. These transporters, expressed respectively in a common parent cell line, LLC-PK$_1$, were used for the evaluation.

TABLE 1A

Inhibition Constants ($K_i$) of Compounds of the Invention

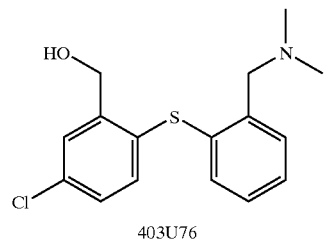

403U76

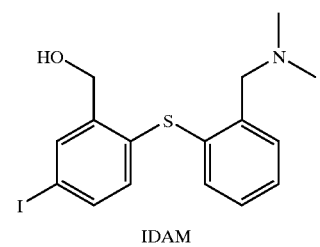

IDAM

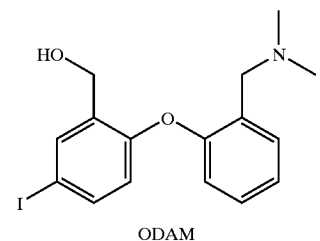

ODAM

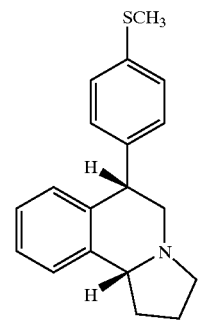

McN(+) 5652

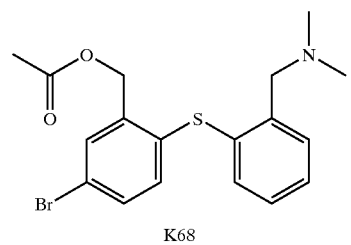

K68

TABLE 1A-continued
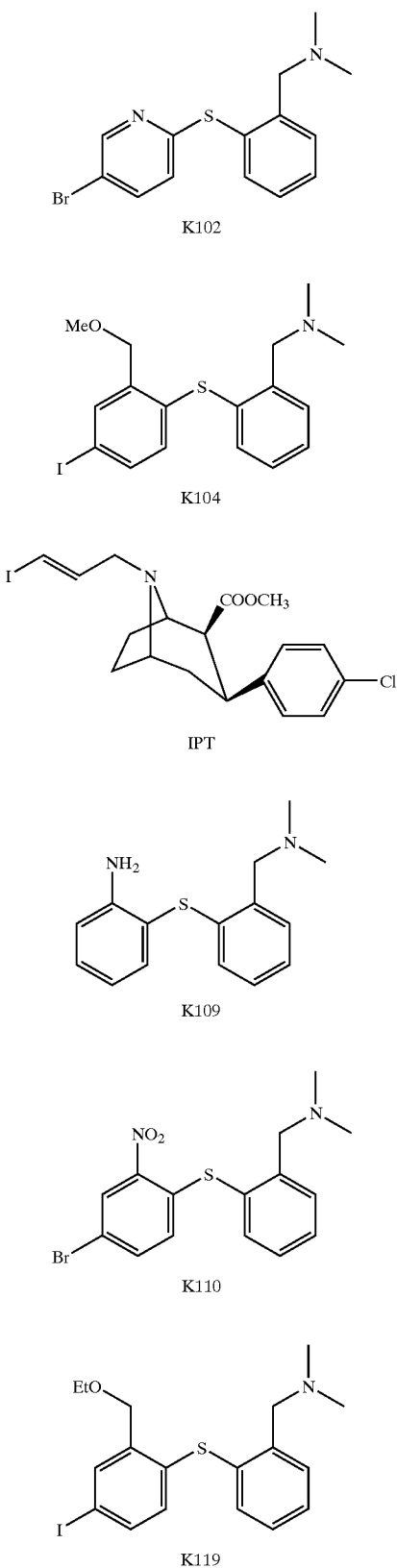
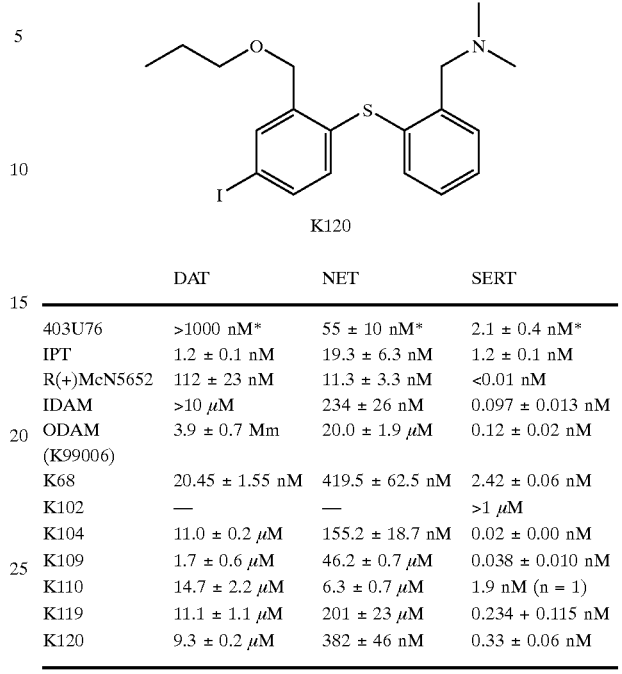
| | DAT | NET | SERT |
|---|---|---|---|
| 403U76 | >1000 nM* | 55 ± 10 nM* | 2.1 ± 0.4 nM* |
| IPT | 1.2 ± 0.1 nM | 19.3 ± 6.3 nM | 1.2 ± 0.1 nM |
| R(+)McN5652 | 112 ± 23 nM | 11.3 ± 3.3 nM | <0.01 nM |
| IDAM | >10 μM | 234 ± 26 nM | 0.097 ± 0.013 nM |
| ODAM (K99006) | 3.9 ± 0.7 Mm | 20.0 ± 1.9 μM | 0.12 ± 0.02 nM |
| K68 | 20.45 ± 1.55 nM | 419.5 ± 62.5 nM | 2.42 ± 0.06 nM |
| K102 | — | — | >1 μM |
| K104 | 11.0 ± 0.2 μM | 155.2 ± 18.7 nM | 0.02 ± 0.00 nM |
| K109 | 1.7 ± 0.6 μM | 46.2 ± 0.7 μM | 0.038 ± 0.010 nM |
| K110 | 14.7 ± 2.2 μM | 6.3 ± 0.7 μM | 1.9 nM (n = 1) |
| K119 | 11.1 ± 1.1 μM | 201 ± 23 μM | 0.234 + 0.115 nM |
| K120 | 9.3 ± 0.2 μM | 382 ± 46 nM | 0.33 ± 0.06 nM |
TABLE 1B
Inhibition Constants (K$_i$) of Compounds of the Invention
Selectivity of IDAM derivatives for monoamine transporters:
DAT, NET and SERT expressed in LLC-PK$_1$ cells
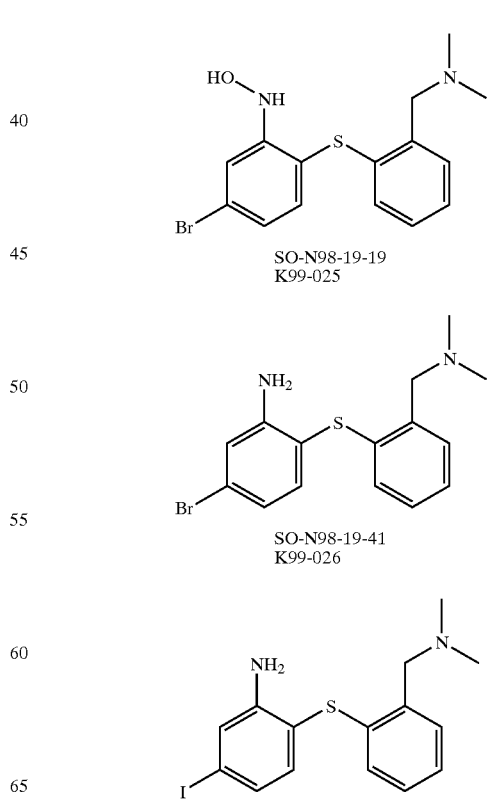

TABLE 1B-continued

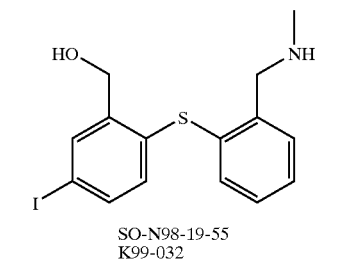

SO-N98-19-55
K99-032

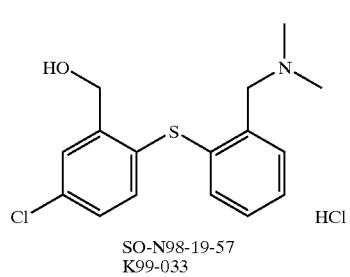

SO-N98-19-57
K99-033

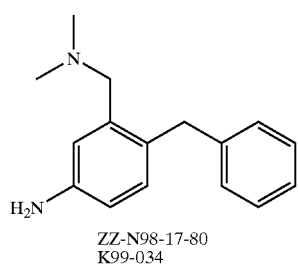

ZZ-N98-17-80
K99-034

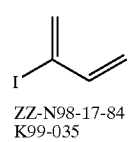

ZZ-N98-17-84
K99-035

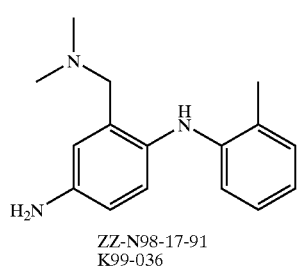

ZZ-N98-17-91
K99-036

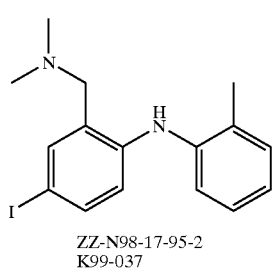

ZZ-N98-17-95-2
K99-037

TABLE 1B-continued

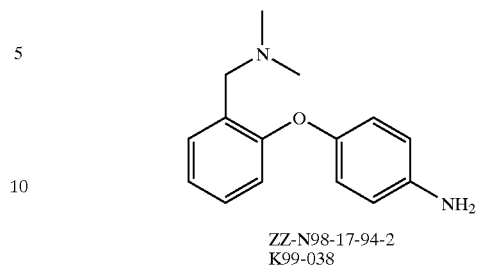

ZZ-N98-17-94-2
K99-038

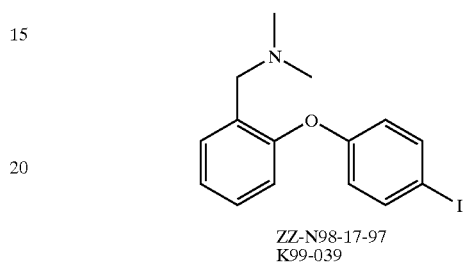

ZZ-N98-17-97
K99-039

|  | DAT | NET | SERT |
|---|---|---|---|
| K99025 |  | 165 ± 9 nM | ~.075 nM |
| K99026 |  | 214 ± 68 nM | ~.022 nM |
| K99028 |  | 699 ± 80 nM | ~.013 nM |
| K99032 |  |  | <0.01 nM |
| K99033 |  |  | <0.01 nM |
| K99034 |  |  | 35.0 ± 2.5 nM |
| K99035 |  |  | 2.8 ± .1 nM |
| K99036 |  |  | 139 ± 15 nM |
| K99037 |  |  | 27.3 ± 6.9 nM |
| K99038 |  |  | — |
| K99039 |  |  | <0.01 nM |

In vitro binding assays were carried out with buffer (50 mM Tris-HCl, pH 7.4, 120 mM NaCl,. 1% BSA) and [$^{125}$I]IPT as the ligand. Membrane preparations of specific transporter: dopamine transporter (DAT), norepinephrine transporter (MET) and serotonin transporter (SERT), expressed in LLC-PK$_1$ cells, respectively were used.

*Values were expressed as IC$_{50}$ for inhibition on substrate uptakes taken from Ferris R. M. et al. "Pharmacological properties of 403U76, a new chemical class of 5-hydroxytryptamine- and nonradrenaline-reuptake inhibitor." *J. Pharm. Pharmacol.* 47:775–781(1995).

In a competition binding assay using [$^{125}$I]IPT as the radioligand for all three monoamine transporters (Kung, M. P. et al., Synapse 20(4):316–324 (1995); Hou, C. et al., Society for Neuroscience Program 28th Annual Meeting, Los Angeles, Calif. [abstract 241.21]:112 (1998)), IDAM, as well as the brominated derivatives, displayed high affinities (K$_i$ values were less than 0.1 nM) for SERT. High K$_i$ values (>10 μM) indicates the lack of binding of these compounds for DAT. The substitution of Br with I appeared to reduce the binding affinity to NET (K$_i$=35.4 nM for the brominated derivative and 234 nM for IDAM). These results suggested that IDAM is superior to the previously reported chlorinated derivative (403U76) (Ferris, R. M. et al., *J. Pharm. Pharmacol* 47:775–781 (1995)) (selectivity shown in Table 1 was expressed as the inhibition on substrate uptakes). (+)McN5652, the selective PET tracer for SERT, was evaluated under similar assay conditions. A selective binding was observed for this compound with K, values of <0.01, 11.3 and 112 nM for SERT, NET and DAT, respectively. Compared to (+)McN5652, IDAM displayed a comparable and even better selectivity profile (less prominent NET binding) for SERT.

In Vitro [$^{125}$I]IDAM Binding Studies

Similar to other SERT ligands, [$^{125}$I]IDAM binding to rat frontal cortical membrane homogenates requires the presence of sodium ion (Na$^+$). There was a rapid increase in specific binding with increasing sodium concentrations up to 100 mM; above that level there was a further gradual increase (about 10%) up to 200 mM concentration. Therefore, subsequent assays were performed using 50 mM Tris-HCl buffer containing 5 mM KCl and 120 mM NaCl.

Specific binding of [$^{125}$I]IDAM to SERT was examined using rat frontal cortical membrane homogenates. The nonspecific binding was defined by using 1 μM paroxetine. Under these conditions, the specific binding was saturable and of high affinity. Scatchard transformation of the binding data gave a linear plot indicating one-site binding (FIG. 1). The mean values from 3 experiments gave a $K_d$ value of 0.25 i 0.05 nM and a $B_{max}$ value of 272±30 fmol/mg protein. The number of binding sites obtained with [$^{125}$I]IDAM is comparable to the values reported with other similar SERT ligands (Kung, M. P. et al., *Life Sci.* 51:95–106 (1992); Mathis, C. A. et al., *Eur. J. Pharmacol* 210(1):103–104 (1992)).

The systematic treatment of rats with p-chloroamphetamine (PCA) is known to reduce the endogenous serotonin level by 90% and cause a concomitant reduction of serotonin neurons in the brain (Kohler. C. et al., *Ann. NY Acad. Sci,* 305:645–663 (1978)). The frontal cortex tissue preparation of rats treated with PCA was used for binding studies of [$^{125}$I]IDAM. Lesions of the serotonergic neuron were induced by systemic injection of PCA, which produced a profound effect on binding to the cortical membrane homogenates prepared from the lesioned animals (FIG. 1). As expected, there was a dramatic reduction of specific binding: the observed $B_{max}$ decreased from 272±30 fmol/mg protein to 20±7 fmol/mg protein with no significant change on the binding affinity ($K_d$).

In Vitro Competition Studies

Figure 2:
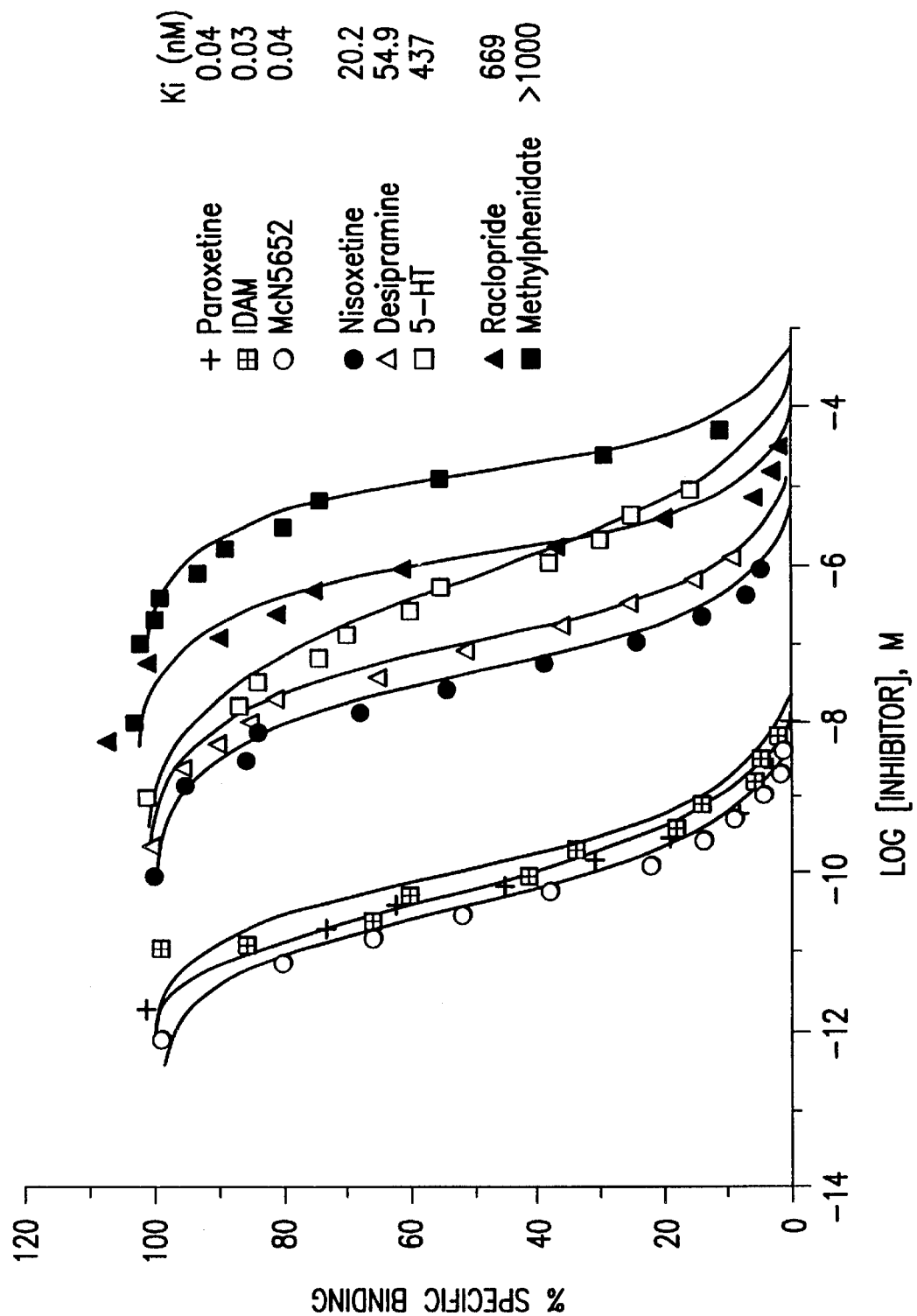
FIG. 2 plots the potencies of compounds to inhibit the specific binding of [$^{125}$I]IDAM to membranes prepared from rat frontal cortical homogenate. Mean values of triplicate determinations are shown in the graph from three independent experiments, each performed in duplicate.

A number of drugs were used in competition binding assays with [$^{125}$I]DAM to characterize the pharmacological profiles of [$^{125}$I]IDAM in rat frontal cortical homogenate. Paroxetine and (+)McN5652, two known selective ligands for SERT, compete effectively with [$^{125}$I]IDAM binding showing Ki values less than 0.1 nM (FIG. 2). The non-radioactive IDAM also showed a high potency in inhibition with a low value ($K_i$=0.08 nM). Drugs such as nisoxetine and desipramine, known selective MET inhibitors, displayed a moderate affinity to compete for [$^{125}$I]IDAM binding (K, =20.2 and 54.9 nM for nisoxetine and desipramine respectively). Whereas 5-HT, the endogenous neurotransmitter, gave a Ki value of 437 nM. Raclopride (a selective dopamine D2/D3 ligand) and methylphenidate (a selective DAT ligand) were much less active in inhibiting [$^{125}$I]IDAM binding ($K_i$, =669 and >1000 nM, respectively).

In Vivo [$^{125}$I]IDAM Binding

Biodistribution off [$^{125}$I]IDAM in different organs, and the brain regions after i.v. injection is shown in Table 2 below. Initial brain uptake at 2 min. post-injection was high (2.44% dose), indicating an efficient passage of the tracer through the intact blood-brain barrier. The optimal lipophilicity of this ligand was reflected by its partition coefficient (PC=473) between n-octanol and phosphate buffer, pH 7.4. The total radioactivity recovered at 2 min post-injection from the major organs was relatively low (less than 60% of total injected dose). The fast clearance of [$^{125}$I]IDAM from the rats suggests that the compound may be rapidly metabolized and excreted into urine. At the later time points, the radioactivity was washed out from the brain with 0.50 and 0.17% dose at 60 and 120 min, respectively. The majority of the radioactivity was washed out from the brain by 4 hr after injection.

Radioactivity levels in all brain regions were the highest at 2 min and then decreased over the 4-hr period. The washout rate was faster in CB, where no SERT binding sites are located, as compared to other brain regions (i.e. ST, HP, CX and HY where different levels of SERT are concentrated). At 30 min post-injection, regions containing serotonergic innervation, that is, ST, HP, CX and HY, showed higher concentrations of radioactivity than CB. The ratio of specific uptake in hypothalamus region ([HY-CBI CB) increased consistently up to 2 hr after injection (Table 2). However, the regional activities appeared to fall rapidly between 60 min and 120 min post-injection. Based on this observation the drug-challenge experiments were performed at 60 min post i.v. injection To investigate the stability of [$^{125}$I]IDAM in rat brain after an i.v. injection, radioactivity associated with hypothalamus region at 60 min post-injection was examined. It was found that only unmetabolized [$^{125}$I]IDAM (>95%) was recovered. No significant detectable metabolites in the brain re-enforces the favorable characteristic of the tracer.

TABLE 2

Biodistribution of radioactivity in rats after an i.v. administration of [$^{125}$I]IDAM.
(average ± SD of three rats in each point)

| Organ | % dose/organ (organ) | | | | |
|---|---|---|---|---|---|
| | 2 min | 30 min | 60 min | 120 min | 240 min |
| BLOOD | 7.619 ± 0.41 | 7.63 ± 1.03 | 6.380 ± 0.729 | 4.160 ± 0.150 | 2.246 ± 0.303 |
| HEART | 1.303 ± 0.10 | 0.27 ± 0.02 | 0.187 ± 0.008 | 0.114 ± 0.023 | 0.048 ± 0.004 |
| MUSCLE | 19.06 ± 8.51 | 16.27 ± 0.82 | 6.775 ± 0.145 | 4.714 ± 0.977 | 2.818 ± 0.208 |
| LUNG | 10.42 ± 1.36 | 1.78 ± 0.08 | 0.931 ± 0.086 | 0.422 ± 0.055 | 0.220 ± 0.018 |
| KIDNEY | 6.54 ± 0.26 | 3.48 ± 0.643 | 1.993 ± 0.351 | 0.832 ± 0.071 | 0.488 ± 0.065 |
| SPLEEN | 0.31 ± 0.08 | 0.279 ± 0.026 | 0.167 ± 0.027 | 0.066 ± 0.008 | 0.024 ± 0.004 |
| LIVER | 6.46 ± 1.18 | 4.709 ± 0.347 | 4.120 ± 0.766 | 2.722 ± 0.308 | 1.469 ± 0.189 |
| SKIN | 3.27 ± 0.48 | 6.121 ± 0.536 | 7.538 ± 0.127 | 6.716 ± 1.304 | 3.851 ± 0.073 |
| BRAIN | 2.44 ± 0.34 | 1.174 ± 0.062 | 0.503 ± 0.027 | 0.168 ± 0.029 | 0.033 ± 0.002 |

| Region | % dose/g (region) | | | | | | | | |
|---|---|---|---|---|---|---|---|---|---|
| | 2 min | SB* | 30 min | SB* | 60 min | SB* | 120 min | SB* | 240 min | SB* |
| CEREBELLUM | 1.377 ± 0.479 | — | 0.416 ± 0.045 | — | 0.153 ± 0.019 | — | 0.053 ± 0.005 | — | 0.012 ± 0.000 | — |
| STRIATUM | 1.377 ± 0.344 | 0.000 | 0.875 ± 0.086 | 1.104 | 0.257 ± 0.042 | 0.673 | 0.105 ± 0.052 | 0.967 | 0.018 ± 0.002 | 0.508 |
| HIPPOCAMPUS | 1.485 ± 0.263 | 0.079 | 0.832 ± 0.048 | 1.002 | 0.355 ± 0.016 | 1.313 | 0.134 ± 0.011 | 1.524 | 0.020 ± 0.003 | 0.705 |

TABLE 2-continued

Biodistribution of radioactivity in rats after an i.v. administration of [$^{125}$I]IDAM.
(average ± SD of three rats in each point)

| | | | | | | | | | | |
|---|---|---|---|---|---|---|---|---|---|---|
| CORTEX | 2.353 ± 0.444 | 0.709 | 0.820 ± .0108 | 0.972 | 0.310 ± 0.060 | 1.024 | 0.89 ± 0.018 | 0.674 | 0.017 ± 0.003 | 0.475 |
| HYPOTHALAMUS | 1.782 ± 0.412 | 0.294 | 0.918 ± 0.113 | 1.208 | 0.422 ± 0.066 | 1.750 | 0.142 ± 0.027 | 1.679 | 0.022 ± 0.011 | 0.865 |

*SB: specific binding = (region-CB)/CB

Pharmacological Specificity of In Vivo [$^{125}$I]IDAM Binding

Figure 3A:
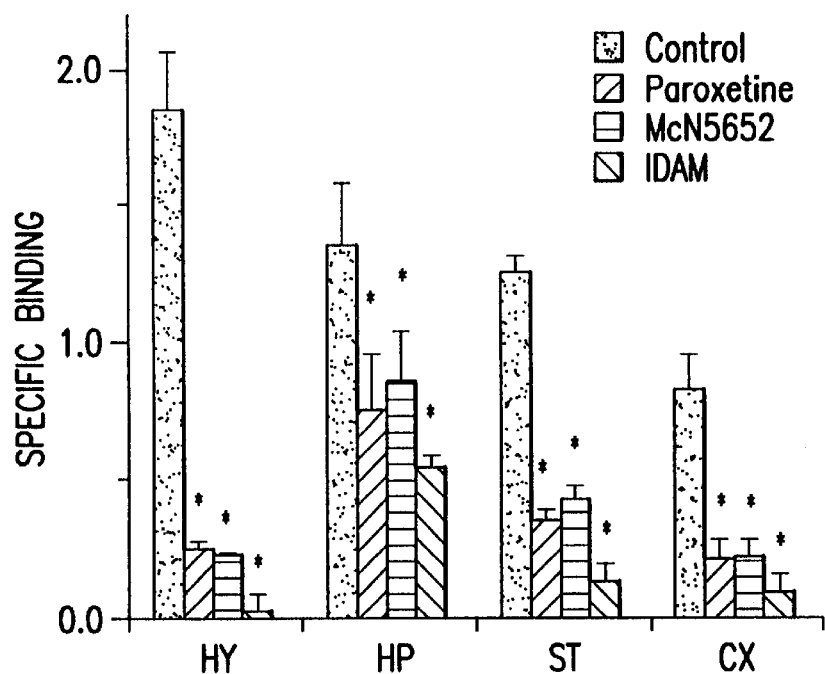
FIGS. 3A and 3B depict the effect of pretreatment with various compounds on specific binding of [$^{125}$I]IDAM in rat brain regions. Rats were pretreated with various drugs at the dose of 2 mg/kg, i.v. 5 min prior to the tracer administration. Sixty minutes after the tracer injection, specific binding in each brain region was compared between saline-pretreated (control) and drug-pretreated rats. Values are presented as the average±SD of three rats in each point * $p<0.05$.
Figure 3B:
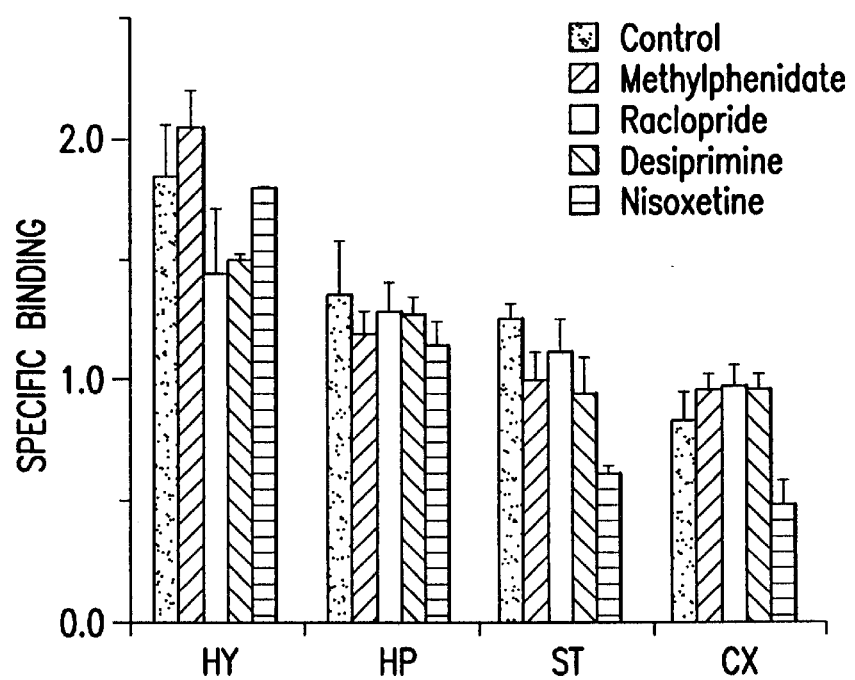

Effects of pretreatment of rats with various compounds on regional brain distribution of [$^{125}$I]IDAM were examined to assess the in vivo pharmacological specificity. Specific binding of [$^{125}$I]IDAM in all brain regions, except HP, was dramatically reduced by pretreatment with paroxetine, (+)McN5652 and IDAM (p<0.05). These results suggest a potent in vivo competition binding of these compounds with [$^{125}$I]IDAM for SERT. The magnitude of blocking in different regions was Hy>CX>ST>HP (FIG. 3). There was a high level of non-specific binding, which could not be blocked by specific SERT ligands, in HP region. Compounds such as methylphenidate (selective for DAT) and raclopride (selective for dopamine D2/D3 receptors) showed no effect on specific uptake, Nisoxetine and desipramine, two selective ligands for NET, showed no significant inhibition on [$^{125}$I]IDAM binding to the brain region, indicating the lack of binding to this tracer to NET sites. Highly selective in vivo binding of SERT observed with [$^{125}$I]IDAM is a very desirable property for a potential SERT imaging agent.

Ex Vivo Autoradiography

At 60 min post-injection of [$^{125}$I]IDAM, autoradiograms of rat brain sections showed intense labeling in several regions (Paxiriog, G. and C. Watson "*The Rat Brain In Stereotaxic Coordinates*," New York Academic Press, (1986)), i.e. olfactory tubercle, lateral septal nucleus, hypothalamic and thalamic nuclei, globus pallidus, central gray, superior colliculus, substantia nigra, interpeduncular nucleus, dorsal and median raphes and locus, coerulus (FIG. 4), areas known to have high densities of SERT sites (Cortes, R. et al., *Neuroscience* 27:473–496 (1988)). Lower but detectable labeling was also found in frontal cortex, caudate putamen, ventral pallidum and hippocampus, areas containing a significantly lower amount of SERT sites. The regional distribution observed with [$^{125}$I]IDAM is consistent with those reported for other SERT ligand (Biegon, A. et al., *Brain Res.* 619:236–246 (1993); Kovachich, G. B. et al., *Brain Res.* 454:78–88 (1988); De Souza E. B. and B. L. Kuyatt, *Synapse* 1:488–496 (1987)) indicating that in vivo nonspecific binding of [$^{125}$I]IDAM is insignificant. In rats pretreated with a high dose of paroxetine (2 mg/kg, i.v.), a selective ligand for SERT, the autoradiograms were significantly reduced as compared to the matched sections of the control rats. The percentage of specific binding varied from more than 95% in interperduncular nucleus, median raphe and dorsomedial hypothalamus to less than 30% in hippocampal regions and several cortical regions. High nonspecific binding (non-paroxetine blockable) observed in HP (more than 70%) observed by ex vivo autoradiogram correlated well with the results obtained using the dissected brain regions (FIG. 3). Autoradiograms of brain sections from nisoxetine-pretreated rats indicated there is no statistically significant difference for labeling of [$^{125}$I]IDAM between control and nisoxetine-pretreated rats. The results further confirm the selective binding of [$^{125}$I]IDAM to SERT sites without concomitant labeling for NET sites.

EXAMPLE 5
Biological Activity of ODAM (Phenoxetine)

Initial biodistribution study in rats (i.v. injection) as performed in Example 4 showed a rapid brain uptake and wash-out (2.03, 1.49, 0.79, 0.27 and 0.07% dose/organ at 2, 30, 60, 120 and 240 min, respectively). More importantly the hypothalamus region where the serotonin neurons are located exhibited a high specific uptake (Table 3). Hypothalamus/cerebellum ratios based on a percentage dose per gram (% dose/g) of these two regions showed values of 1.22, 1.86, 1.86, 1.63 and 1.34 at 2, 30, 60, 120 and 240 min, post i.v. injection, respectively. However, regional brain localization is not a clear cut as those of IDAM.

TABLE 3

Biodistribution in rats after an i.v. injection of [$^{125}$I]ODAM
(% dose/organ, avg of 3 rat ± SD)

| Organ | 2 min | 30 min | 60 min | 120 min | 240 min |
|---|---|---|---|---|---|
| BLOOD | 3.009 ± 0.212 | 3.517 ± 0.504 | 3.296 ± 0.373 | 1.868 ± 0.186 | 0.976 ± 0.073 |
| BRAIN | 2.033 ± 0.087 | 1.489 ± 0.146 | 0.785 ± 0.231 | 0.267 ± 0.066 | 0.065 ± 0.017 |
| THYROID | 0.080 ± 0.019 | 0.039 ± 0.006 | 0.028 ± 0.005 | 0.034 ± 0.006 | 0.041 ± 0.038 |

Regional brain distribution (ratio/CB)

| Region | 2 min | 30 min | 60 min | 120 min | 240 min |
|---|---|---|---|---|---|
| CEREBELLUM | 1.000 | 1.000 | 1.000 | 1.000 | 1.000 |
| STRIATUM | 0.906 | 1.590 | 1.605 | 1.617 | 1.539 |
| HIPPOCAMPUS | 0.983 | 1.563 | 1.791 | 1.846 | 1.648 |
| CORTEX | 1.436 | 1.771 | 1.690 | 1.672 | 1.322 |
| HYPOTHALAMUS | 1.221 | 1.860 | 1.858 | 1.630 | 1.343 |

PC:305; 1-octanol/0.1M KH$_2$PO$_4$ buffer, pH 7.4

Initial binding study using frontal cortex membrane homogenates of rat brain (see Example 4) and [$^{125}$I]IDAM as the ligand showed that the ODAM displayed a very good binding affinity for SERT ($K_i$=2.88±0.88 nM).

Using the membrane preparations containing specific monoamine transporter: DAT, NET and SERT expressed in LLC-PK$_1$ cells, respectively, the inhibition constant of IDAM and ODAM were determined and are listed in Table 4. It appears that IDAM is more potent and selective to SERT. However, the in vivo biodistribution data in rats and the SPECT imaging study suggest that ODAM displayed a higher brain uptake and slower clearance from the target area.

Table 4 is a comparison of inhibition constants (K$_i$) of IDAM and ODAM using in vitro binding assays and membrane preparations containing specific monoamine transporters: DAT, NET and SERT expressed in LLC-PK$_1$ cells, respectively.

TABLE 4

Comparison of Inhibition Constants (K$_i$) of IDAM and ODAM

| | DAT | NET | SERT |
|---|---|---|---|
| IDAM | >10 μM | 234 ± 26 nM | 0.097 ± 0.013 nM |
| ODAM | 3.9 ± 0.7 μM | 20.0 ± 1.9 nM | 0.12 ± 0.02 nM |

EXAMPLE 6

SPECT Imaging in Baboons

The acquisition of SPECT images were obtained by a triple-head gamma camera equipped with ultra high resolution fan-beam collimators (Picker Prism 3000). The acquisition parameters comprised of a rotational radius of 14 cm, a 15% energy window centered on 159 KeV, 120 projection angles over 360 degrees, and a 128, ×128 matrix with a pixel width of 2.11 mm in the projection domain. Data collection started at immediately after iv. injection of 555 MBq (15 mCi) of [$^{123}$I]IDAM. Forty-eight 5-minute scans were carried out over a total time period of 240 min. The projection images were reconstructed by filtered-back projection. Then, a 3D, low pass Butterworth filter was applied. For uniform attenuation correction, Chang's first order method was used. A summed data between 60–120 min after injection of [$^{123}$I]IDAM were used to provide transverse, coronal and saggital views of SPECT images of the baboon head.

Figure 5:
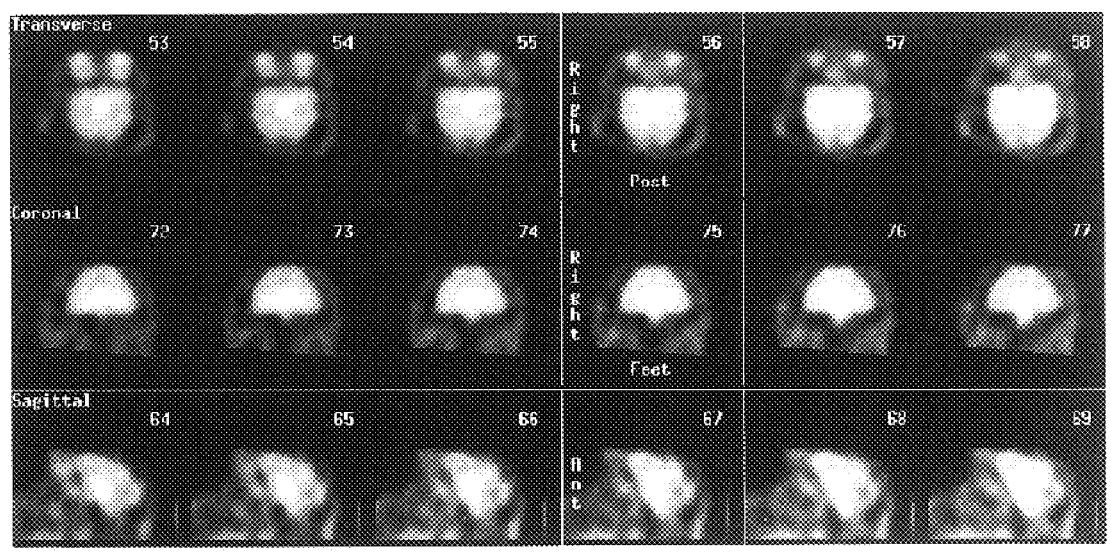
FIG. 5 depicts transverse, coronal and saggital views of SPECT (upper row) images of the baboon head. The SPECT image represents the summed counts acquired 60–120 min after injection of [$^{123}$I]IDAM. A high concentration of activity was localized in the midbrain area (MB: raphe nucleus, substantia nigra and hypothalamus) where SERT is highly concentrated.

The SPECT imaging study of [$^{125}$I]IDAM in the brain of a baboon by SPECT, at 60–120 min after injection, showed an excellent contrast in the midbrain area (raphe nucleus, substantia nigra, hypothalamus), where a high density of SERT is concentrated (FIG. 5). Coregistration with MRI was used for the identification of the anatomical structure and resulted in the expected localization of this tracer. The image observed with [$^{125}$I]IDAM showed a very good correlation with the picture obtained with the PET imaging agent [$^{11}$C](+)McN5652.

Figure 8B:
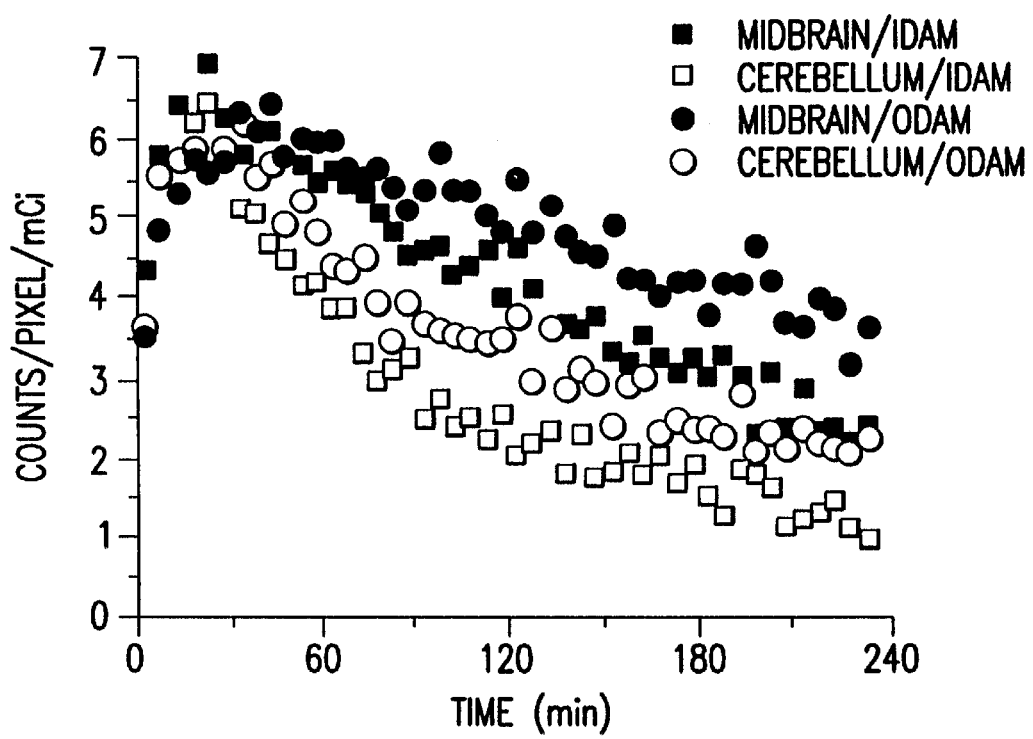
FIG. 8B depicts time-activity curves for the midbrain and cerebellum for both [$^{123}$I]IDAM and [$^{123}$I]ODAM (both in the same baboon).
Figure 7:
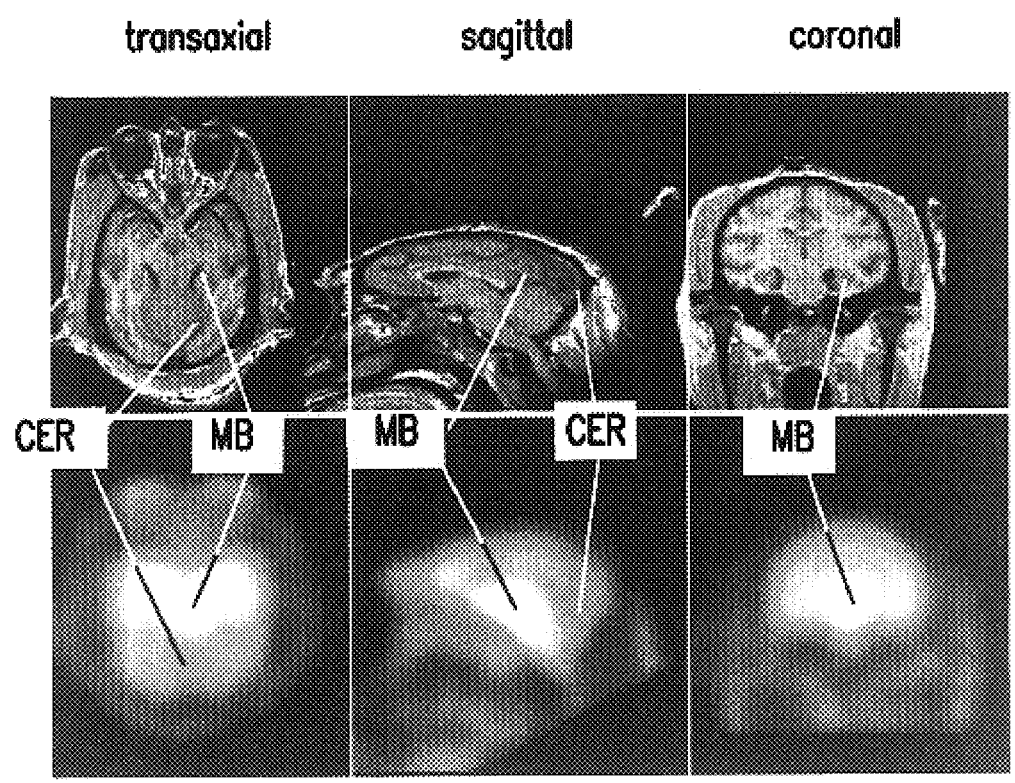
FIG. 7 depicts a comparison of MRI images (anatomy) and SPECT images of [$^{123}$I]IDAM (SERT localization), presented in transaxial, sagittal and coronal views (between 60–120 minutes post-i.v. injection). [$^{123}$I]IDAM localized with high concentration in midbrain (MB, raphe nucleus, substantia nigra, hypothalamus) where the SERT concentration is high; it displayed no specific uptake in cerebellum (CER) an area lacking SERT. The ratio of MB/CER uptake at 120 minutes was 2.4.
Figure 8A:
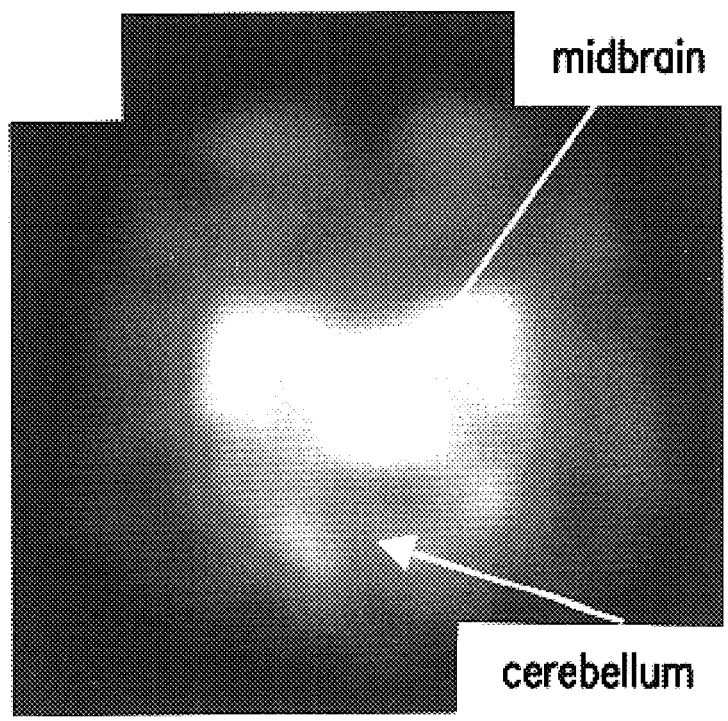
FIG. 8A depicts a summed transverse image at the point of pseudo-equilibrium (approx. 90–120 min post-injection) approximately at the level of the midbrain.

SPECT images of [$^{123}$I]ODAM binding to serotonin transporters in a baboon's brain and the time activity curves were obtained in a similar manner (FIG. 8A). The SPECT images obtained approximately at the level of the midbrain at 90–120 min post-injection were very similar to those obtained with [$^{123}$I]IDAM.

Time-activity curves for the midbrain and cerebellum for both [$^{123}$I]IDAM and [$^{123}$I]ODAM (both in the same baboon) were compared (FIG. 8B). The counts have been corrected for injected dose, so they should represent approximately the amount of relative brain uptake between the two tracers. [$^{123}$I]ODAM appears to have a higher brain uptake, and slower kinetics than [$^{123}$I]DAM, possibly reflecting the slower metabolism expected for the newer tracer. Compared with [$^{123}$I]IDAM, the total integrated brain uptake (area under the time-activity curves extrapolated to t=∞) is 46% higher in the cerebellum and 58% higher in the midbrain for [$^{123}$I]ODAM. The kinetics of uptake and retention of ODAM in the brain displays different rates as compared with those of [$^{123}$I]IDAM.

FIG. 8A depicts a summed transverse image at the point of pseudo-equilibrium (approx. 90–120 min post-injection) approximately at the level of the midbrain.

FIG. 8B depicts time-activity curves for the midbrain and cerebellum for both [$^{123}$I]IDAM and [$^{123}$I]ODAM (both in the same baboon).

Discussion of In Vitro and In Vivo Results

A novel radioiodinated compound, [$^{125}$I]IDAM, for mapping SERT in the brain was successfully evaluated. Initial studies on the binding selectivity of IDAM for three monoamine transporters (SERT, DAT and NET) were performed in LLC-PK$_1$ cells (expressing one of the three monoamine transporters, respectively) (Gu, H. et al., *J. Biol. Chem.* 269(10):7124–7130 (1994)). IDAM displayed an excellent binding to SERT sites (K$_i$=0.097 nM) and showed a better selectivity for SERT (more than 1,000 fold), as compared to the corresponding chlorinated and brominated derivatives (Table 1). The lower affinity of IDAM for NET (K$_i$=234 nM) makes it highly desirable as a selective SPECT imaging agent for SERT. The selectivity for SERT demonstrated by IDAM is is similar or even better than that of (+)McN5652. This unique characteristic plus an optimal lipophilicity displayed by this tracer (partition coefficient= 473; 1-octanol/pH 7 buffer) makes this tracer a suitable candidate for a SERT tracer for SPECT imaging.

The binding affinity of this ligand was measured in a native tissue homogenate system, by using rat frontal cortical membranes, to which a high binding affinity of [$^{125}$I] IDAM (K$_d$=0.2 nM) was observed. In addition, [$^{125}$I]IDAM displayed a lower nonspecific binding (<5% at K$_d$ value) as compared to another radioiodinated ligand, 4-I-tomoxetine, (>25% at value; K$_d$=0.04 nM) (Kung, M. P. et al., *Life Sci.* 51:95–106 (1992)). Several lines of evidence suggest that the specific [$^{125}$I]IDAM binding to rat cortical membranes is indeed associated with SERT. First, [$^{125}$I]IDAM binding to rat cortical membranes was inhibited effectively and completely by known SERT ligands, such as paroxetine and (+)McN5652 with Ki values in low nanomolar range. Drugs labeling the other two monoamine transporters, such as nisoxetine or desipramine (NET selective) and methylphenidate (DAT selective) were much less potent in inhibiting [$^{125}$I]IDAM binding to the cortical membrane preparation (FIG. 2). Second, destruction of serotonergic neurons by PCA resulted in a 90% loss of [$^{125}$I]IDAM binding to rat cortical membranes (FIG. 1), showing the ligand is specifically bound to the serotonergic neuron, on which the SERT binding sites are located.

In the in vivo biodistribution studies, a high accumulation of radioactivity in the rat-brain after an i.v. administration of [$^{125}$I]IDAM was observed (2.44% of injected dose at 2 min post-injection), indicating its excellent ability to penetrate the blood-brain barrier. This is most likely due to the optimal lipophilicity displayed by this tracer (partition coefficient= 473). A significant amount of the injected [$^{125}$I]IDAM can be delivered to the target sites in the brain, which fulfills the first requirement as an useful imaging agent. At 60 min post-injection of [$^{125}$I]IDAM the regional distribution of radioactivity in the brain correlated well with the serotonergic innervation throughout the rat brain. Since the cerebellum region receives a minimal serotonin innervation (Hrdina, P. D. et al., *J. Pharmacol. Exp. Ther.* 252(1):410418 (1990)), low radioactivity associated with cerebellum reflects the low in vivo nonspecific binding of [$^{125}$I]IDAM. The values of specific regional binding (SB) expressed as ratios [(region-CB)/CB] were excellent (see Table 2). These ratios obtained with [$^{125}$I]IDAM in hypothalamus region appear to be slightly lower than those reported for [$^{11}$C](+) McN5652 (3.6 at 90 min) or [$^{123}$I]5-I-6-NO$_2$-quipazine (4.0 at 2 to 6 hr) (Biegon, A. et al., *Brain Res.* 619:236–246 (1993)). The lower ratio (1.75 at 60 min) could be due to the limitation on the precision of dissecting small and discrete areas containing enriched SERT in the rat brain. The ratios reported from different laboratories are highly operator-dependent. Nevertheless, it is demonstrated that the specific localization of [$^{125}$I]IDAM in brain regions correlated well with the serotonergenic terminal distribution. The nature of specific regional binding of [$^{125}$I]IDAM, predominately in hypothalamus region, is further validated by competition studies. Virtually all of the selective binding (SB), as indicated by (HY-CB)/CB ratio, is blocked by a pretreatment with specific SERT ligands. i.e. paroxetine or (+)McN5652, (FIG. 3) suggesting [$^{125}$I]IDAM is competing with these blockers for the same SERT sites. As expected, pretreatment with agents showing no SERT affinity did not affect the regional distribution of [$^{125}$I]IDAM in the rat brain. The in vivo pharmacological specificity of [$^{125}$I]IDAM for SERT in the rat brain is well depicted in the present study.

The kinetics of in vivo [$^{125}$I]IDAM binding to SERT sites in the rat brain was found to be relatively fast, approaching the optimal ratio (target vs. non-target) as early as 30 min post-injection. A rapid clearance from the brain regions was observed with a half-time of less than 60 min. In the present study with rats, a moderate peak ratio [SB=1.75 of (HY—CB)/CB] was observed. Despite the fast peripheral metabolism, clearance and the moderate target vs. nontarget ratio observed with [$^{123}$I]IDAM in rats, the preliminary imaging studies with [$^{125}$I]IDAM/SPECT in baboons resulted in an excellent contrast and clearly reflected the known pattern of distribution of SERT in the brain of baboons (FIG. 5). In conclusion, radioiodinated IDAM is a selective in vivo and in vitro ligand for SERT. This novel tracer, which demonstrated a high affinity, excellent selectivity and good brain penetration, has excellent characteristics for SPECT imaging of SERT in the brain.

Having now fully described this invention it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

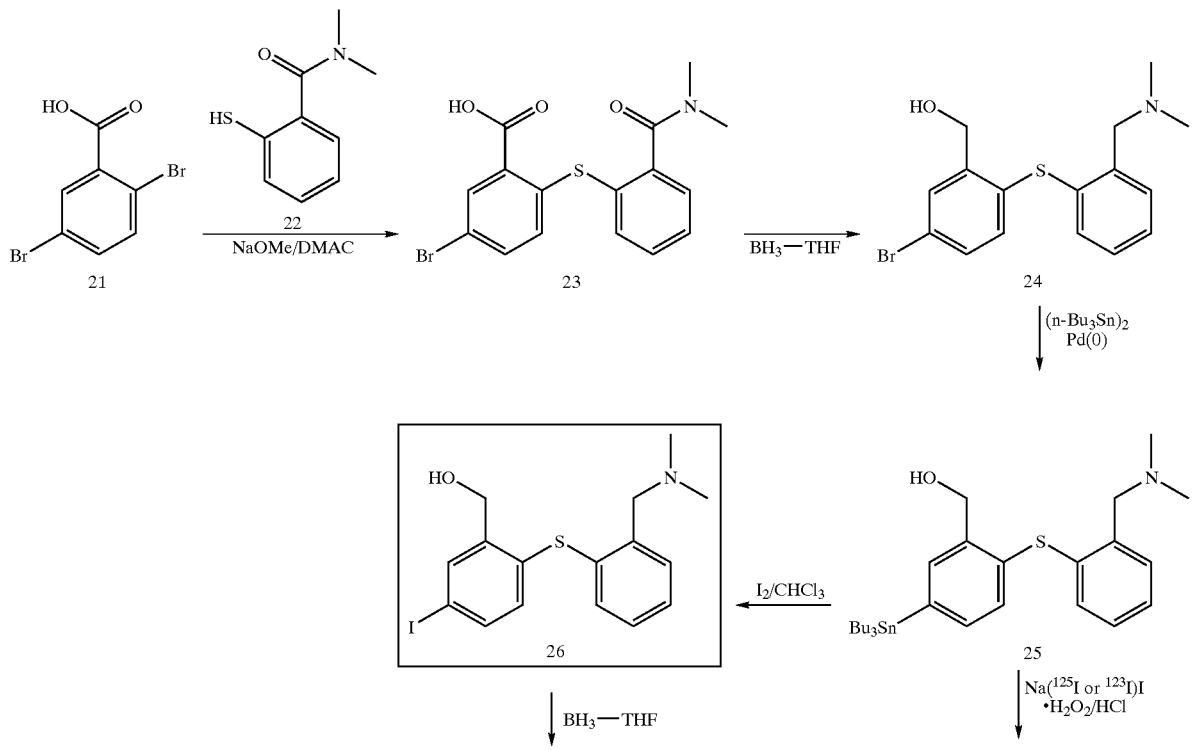

Scheme 1

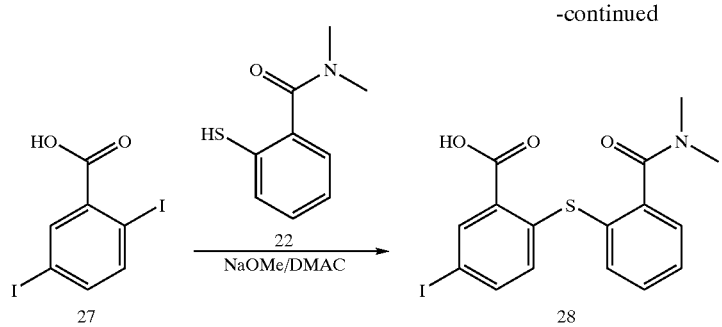
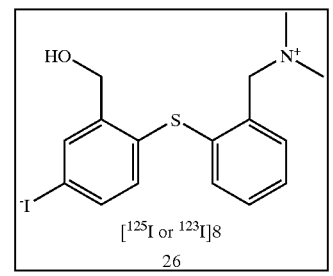
Scheme 2
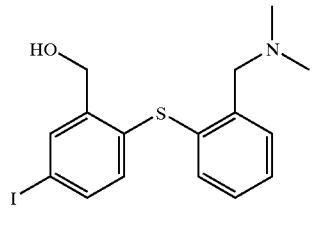
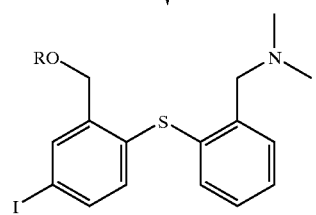
Scheme 3
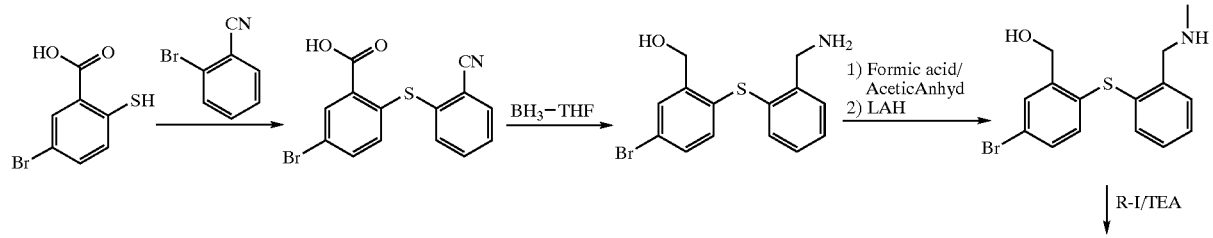

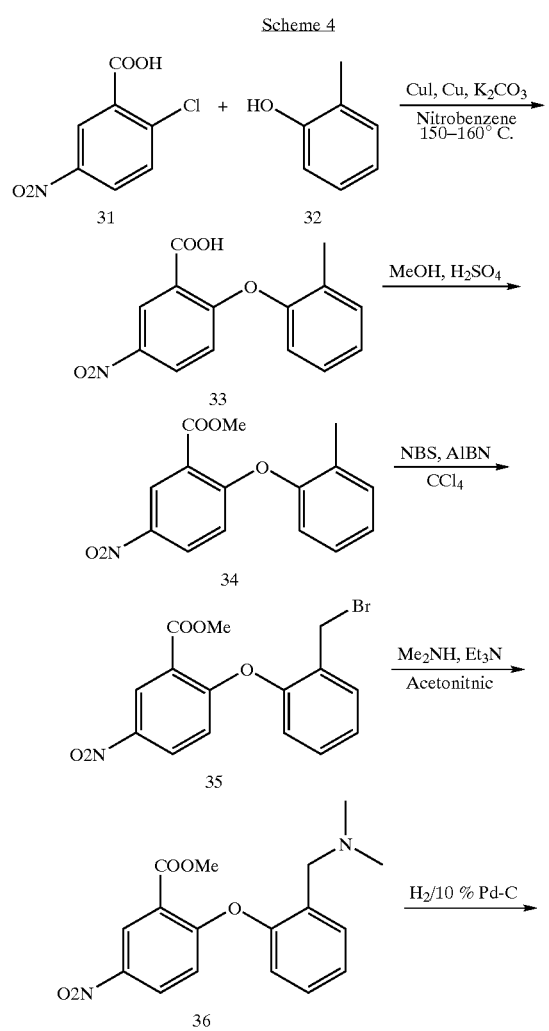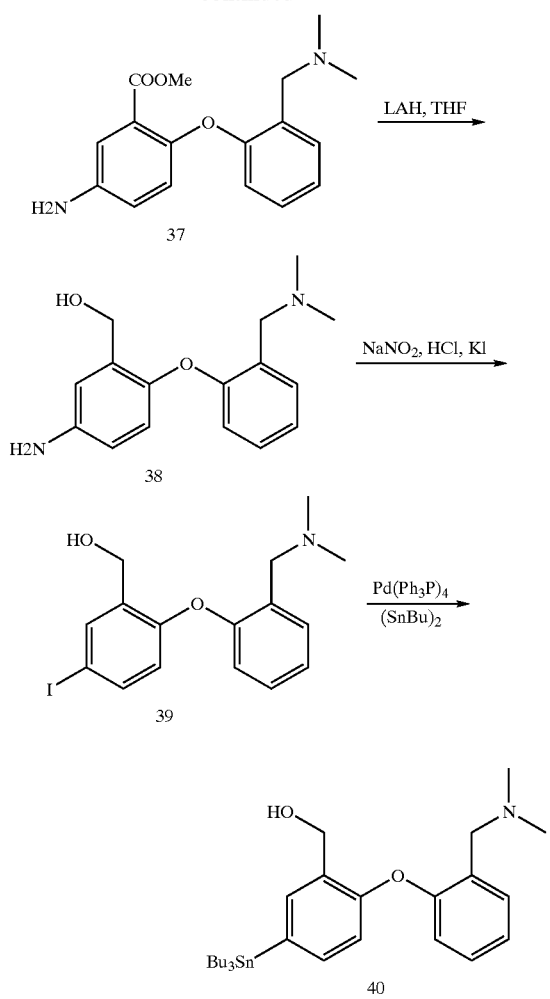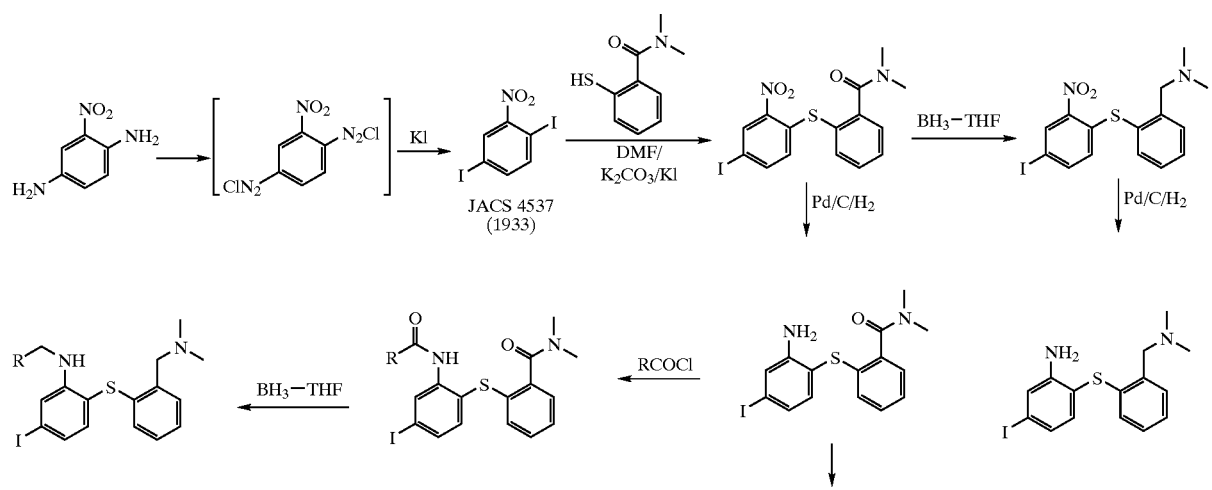

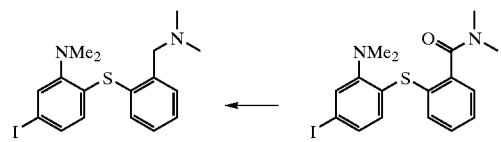
Scheme 6
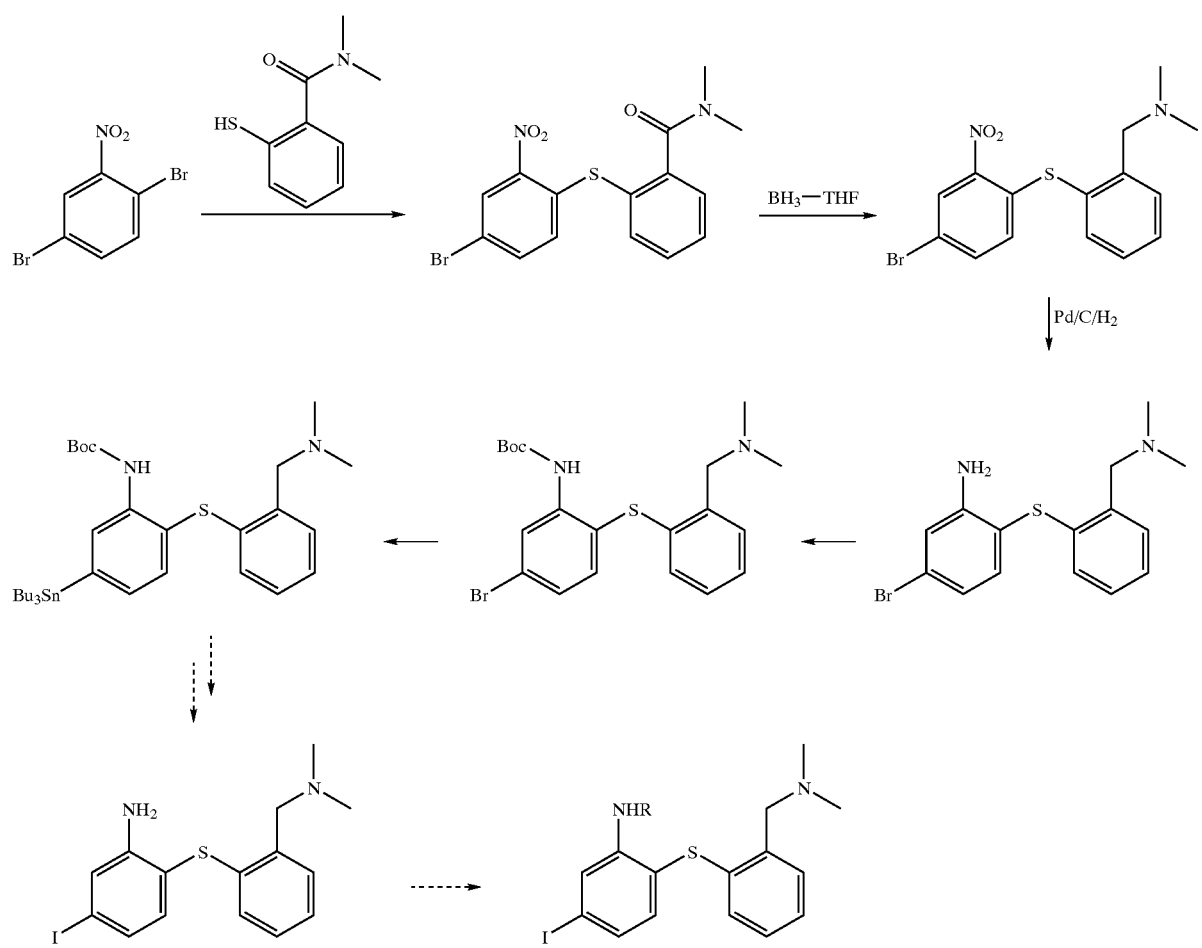
Scheme 7
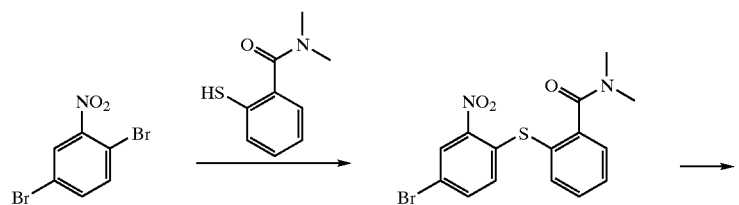

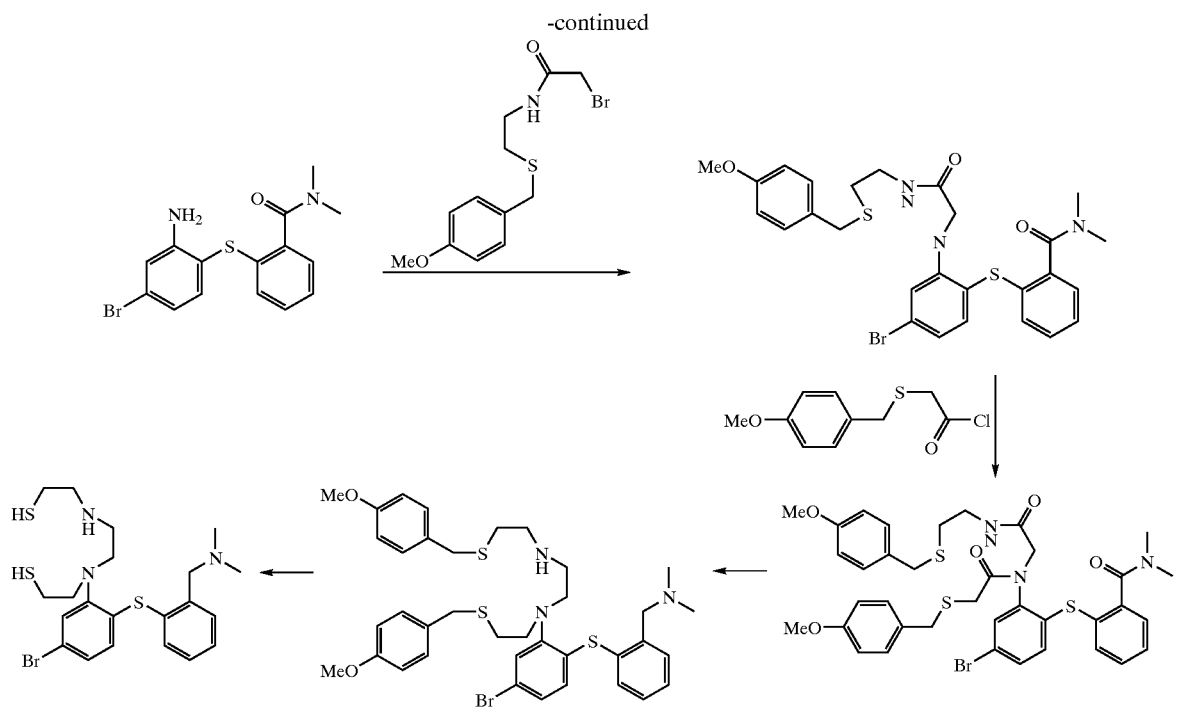
Scheme 8
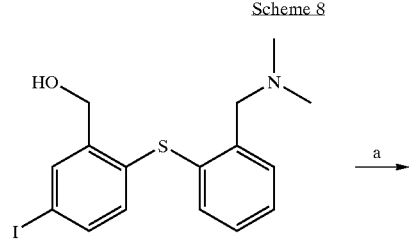
a
a) 1) RuCl$_2$[P(C$_6$H$_5$)$_3$]$_3$, t-C$_4$H$_9$OOH, 2)H$^+$
   or 1) BrCN, 2) HCl
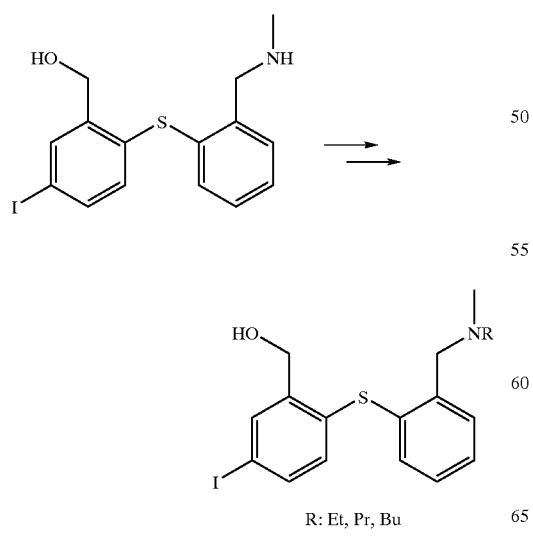
R: Et, Pr, Bu
Scheme 9
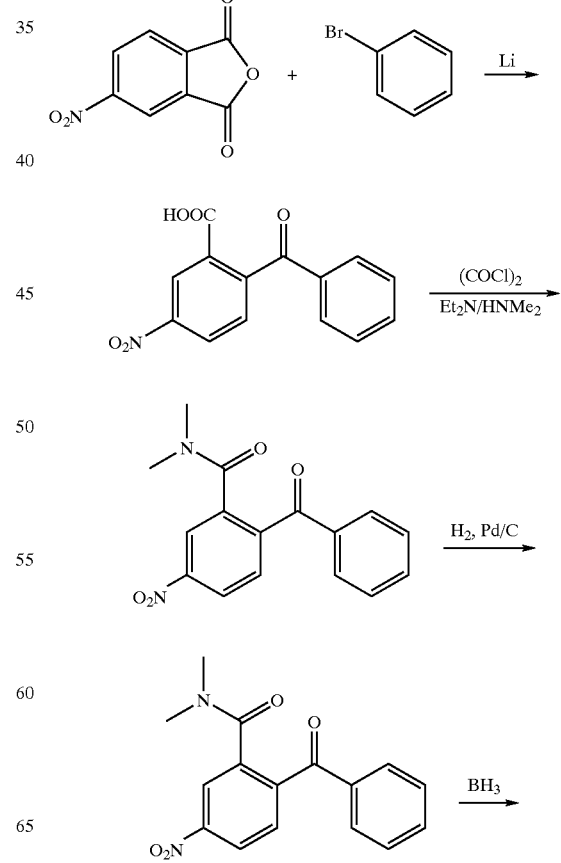

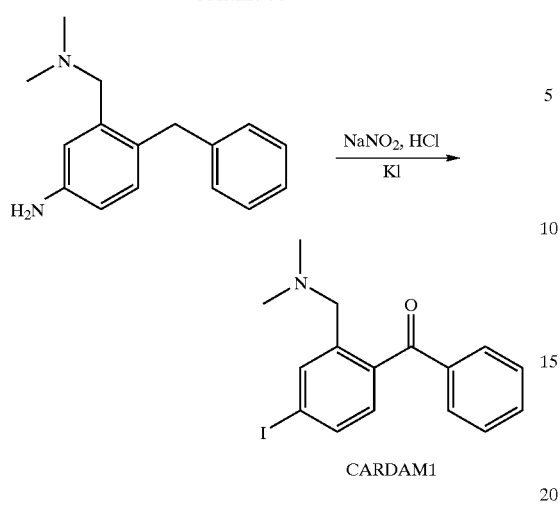
CARDAM1
Scheme 10
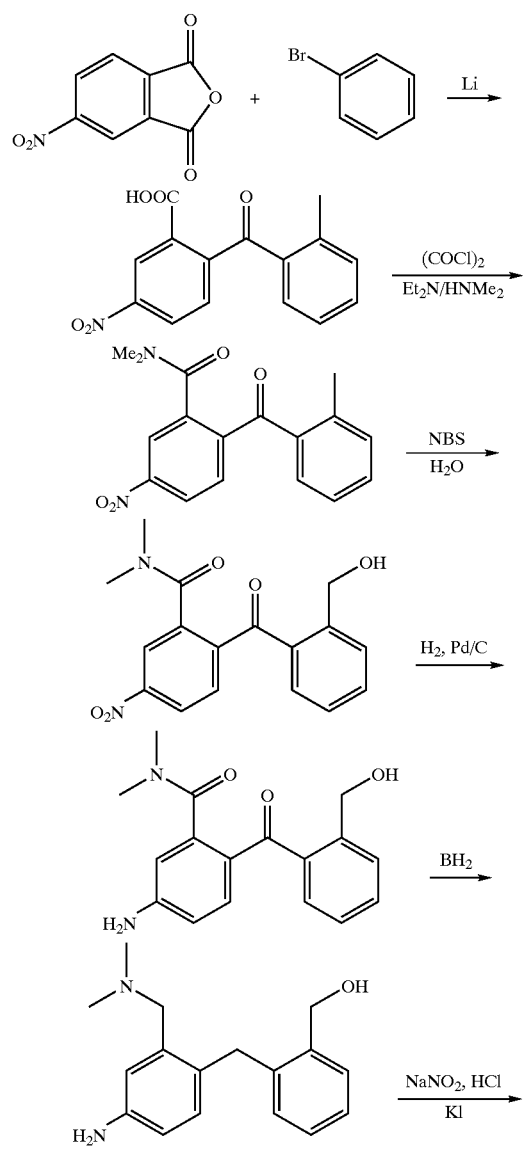
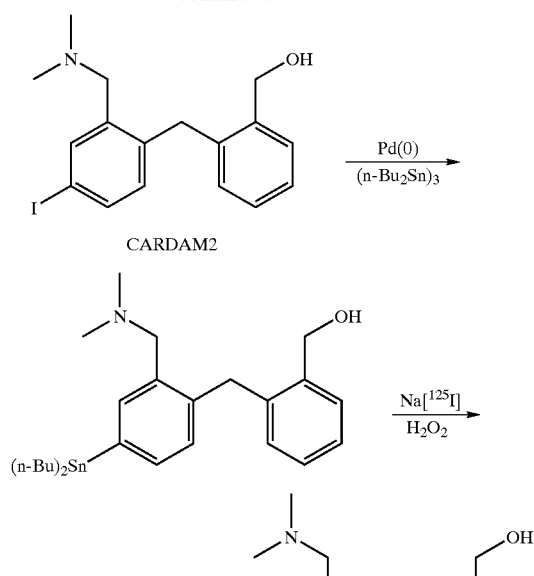
CARDAM2
Scheme 11
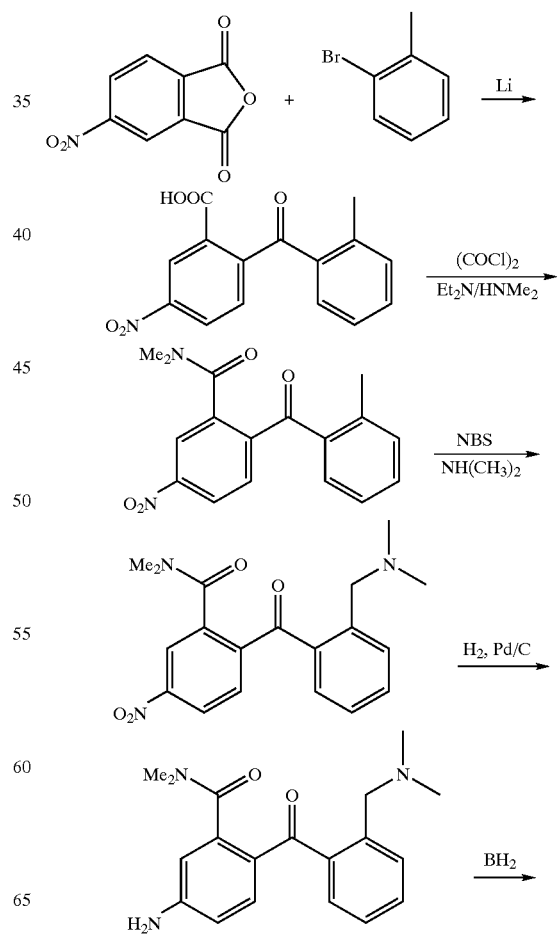

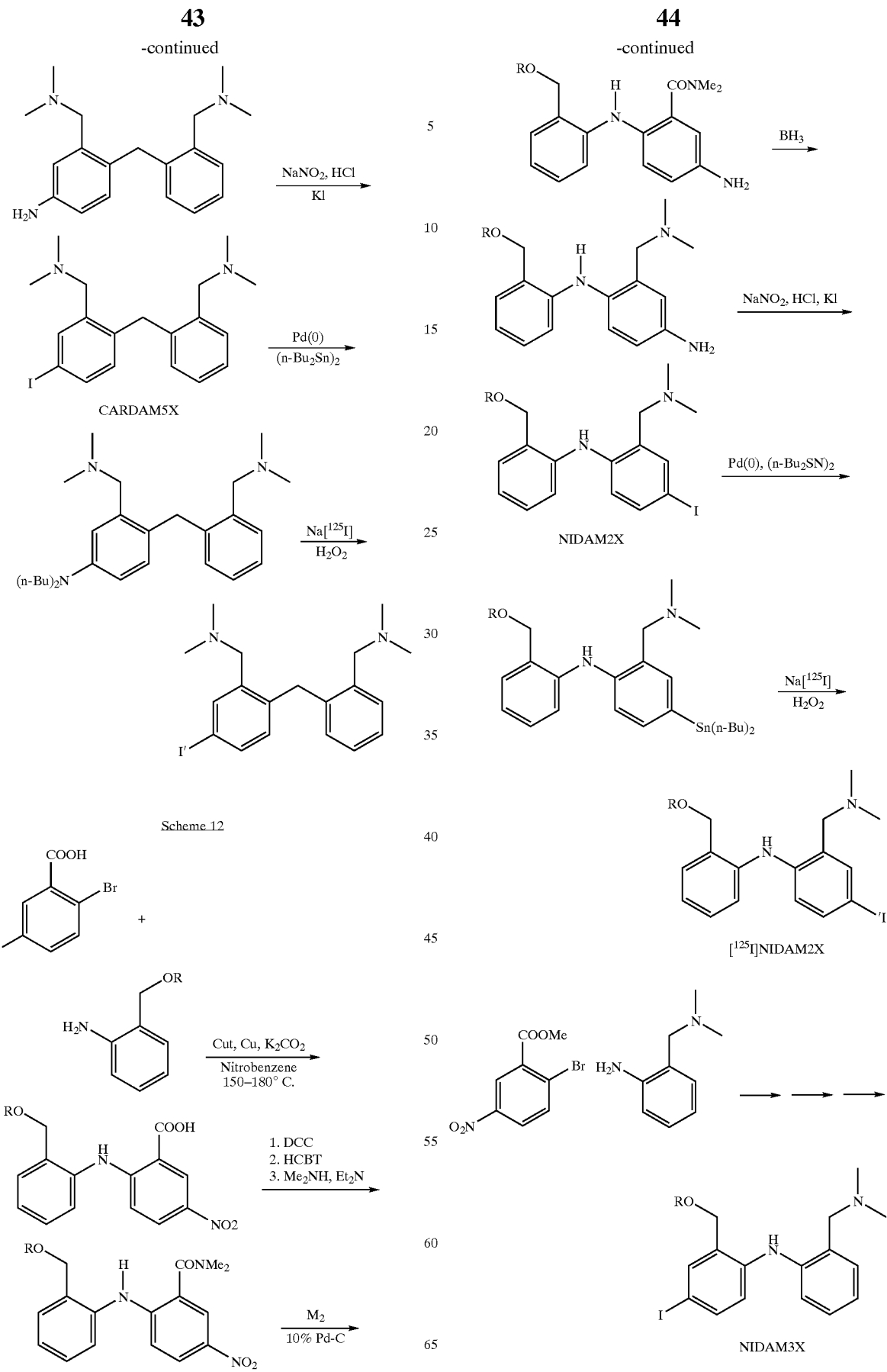

Scheme 13

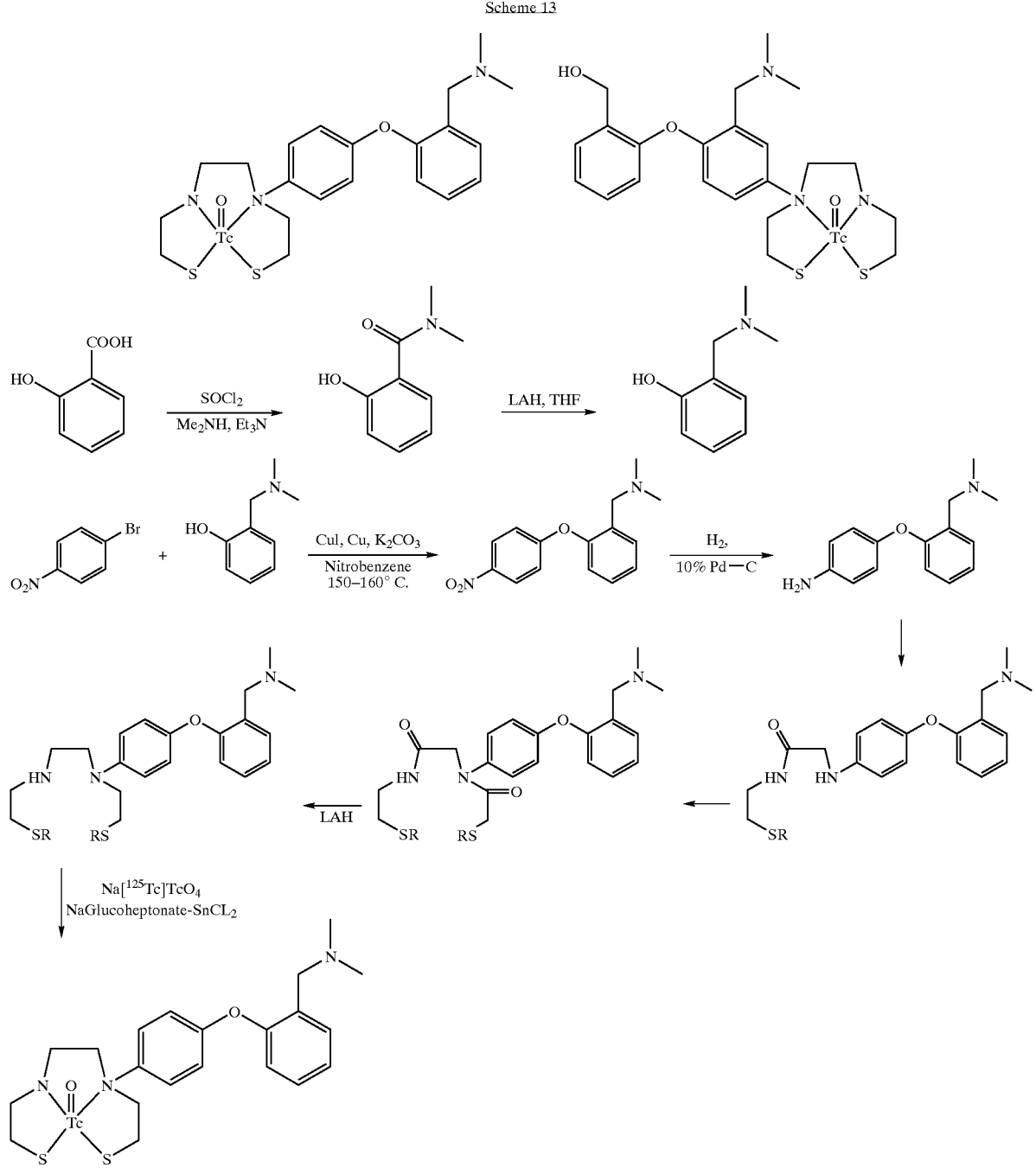

What is claimed is:
1. A compound of Formula I:

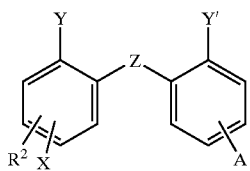

or a pharmaceutically acceptable salt thereof; wherein

X is hydrogen, Cl, Br, I, $NO_2$, or $NR^3R^4$;

Y is hydrogen, —$CH_2OR^5$, —$CH_2NCH_3R^1$, $NO_2$, or $NR^3R^4$;

Y' is hydrogen, —$CH_2OR^5$, —$CH_2NCH_3R^1$, $NO_2$, or $NR^3R^4$; provided that at least one of the Y or Y' is —$CH_2NCH_3R^1$;

Z is S, or O;

A is hydrogen, Cl, I, or Br;

$R^1$ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, or naphthylmethyl;

$R^2$ is hydrogen or methyl;

R³ and R⁴ are independently hydrogen, hydroxy, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, or naphthylmethyl;

R⁵ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, or naphthylmethyl;

R⁶ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl, or naphthylmethyl; and R⁷ and R⁸ are independently hydrogen, $C_1$–$C_5$ alkyl or chloro;

with the proviso that one or both of X or A is selected from the group consisting of $^{123}$I, $^{131}$I, $^{125}$I, $^{77}$Br and $^{76}$Br.

2. A compound of claim 1, wherein

X is selected from the group consisting of $^{123}$I, $^{131}$I, $^{125}$I, $^{77}$Br and $^{76}$Br;

Y is —CH₂OR⁵, NO₂ or NR³R⁴;

A is hydrogen;

R¹ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R² is hydrogen or methyl;

R³ and R⁴ are independently hydrogen, hydroxy, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R⁵ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R⁶ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl; and R⁷ and R⁸ are independently hydrogen, $C_1$–$C_5$ alkyl or chloro.

3. A compound of claim 1, wherein

X is hydrogen, Cl, Br, I, NO₂ or NR³R⁴;

Y is —CH₂OR⁵, NO₂ or NR³R⁴;

A is selected from the group consisting of $^{123}$I, $^{131}$I, $^{125}$I, $^{77}$Br and $^{76}$Br;

R¹ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R² is hydrogen or methyl;

R³ and R⁴ are independently hydrogen, hydroxy, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R⁵ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl;

R⁶ is hydrogen, $C_1$–$C_5$ alkyl, $C_3$–$C_8$ cycloalkyl, $C_{1-5}$ alkylcarbonyl, ($C_3$–$C_8$ cycloalkyl)carbonyl, phenyl, benzyl, naphthyl or naphthylmethyl; and R⁷ and R⁸ are independently hydrogen, $C_1$–$C_5$ alkyl or chloro.

4. A compound of claim 2, wherein X is a radioactive isotope selected from the group consisting of $^{123}$I, $^{131}$I, and $^{125}$I.

5. A compound of claim 4, wherein X is $^{123}$I.

6. A compound of claim 3, wherein A is a radioactive isotope selected from the group consisting of $^{123}$I, $^{131}$I, and $^{125}$I.

7. A compound of claim 6, wherein A is $^{123}$I.

8. A compound of claim 1, having the general formula:

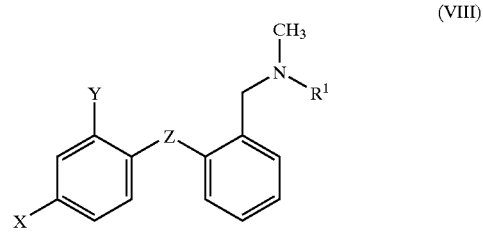

(VIII)

or

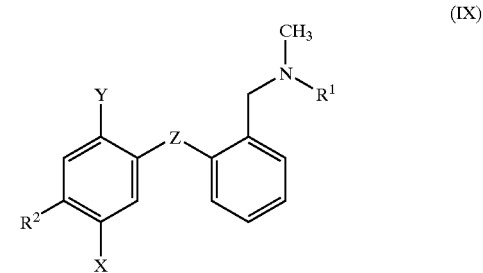

(IX)

or a pharmaceutically acceptable salt thereof, where

X is selected from the group consisting of $^{123}$I, $^{131}$I, $^{125}$I, $^{77}$Br and $^{76}$Br;

Y, Z and R¹ and R² are as defined as in claim 1.

9. A compound of claim 8, wherein:

Y is —CH₂OH; —CH₂OCH₃; —NHR⁴, where R⁴ is hydrogen, hydroxy or $C_{1-5}$ alkyl; —NO₂; or —CH₂OC(O)CH₃; and R¹ is methyl.

10. A compound of claim 9, wherein X is selected from the group consisting of $^{123}$I, $^{131}$I, and $^{121}$I.

11. A compound of claim 8, wherein:

Y is —CH₂OH; —CH₂OCH₃; —NH₂, or —OH;

Z is S; and

R¹ is hydrogen or methyl.

12. A compound of claim 8, having the formula VIII, wherein:

X is selected from the group consisting of $^{123}$I, $^{131}$I and $^{125}$I;

Y is —NH₂;

Z is —S—; and

R¹ is methyl.

13. A compound of claim 8, having the formula VIII, wherein:

X is selected from the group consisting of $^{123}$I, $^{131}$I and $^{125}$I;

Y is —CH₂OH;

Z is —S—; and

R¹ is methyl.

* * * * *